US011723913B2

United States Patent
Prince El Adnani et al.

(10) Patent No.: US 11,723,913 B2
(45) Date of Patent: Aug. 15, 2023

(54) USE OF SPECIFIC SIRNA AGAINST PROTEIN S FOR THE TREATMENT OF HEMOPHILIA

(71) Applicant: UNIVERSITÄT BERN, Bern (CH)

(72) Inventors: Raja Prince El Adnani, Bern (CH); Anne Angelillo-Scherrer, Fribourg (CH)

(73) Assignee: Universität Bern, Bern (CH)

( * ) Notice: Subject to any disclaimer, the term of this patent is extended or adjusted under 35 U.S.C. 154(b) by 198 days.

(21) Appl. No.: 16/760,474

(22) PCT Filed: Nov. 2, 2017

(86) PCT No.: PCT/EP2017/078107
§ 371 (c)(1),
(2) Date: Apr. 30, 2020

(87) PCT Pub. No.: WO2019/086117
PCT Pub. Date: May 9, 2019

(65) Prior Publication Data
US 2020/0345757 A1 Nov. 5, 2020

(30) Foreign Application Priority Data
Nov. 1, 2017 (WO) .................. PCT/EP2017/077986

(51) Int. Cl.
C07H 21/02 (2006.01)
C07H 21/04 (2006.01)
A61K 31/713 (2006.01)
C12N 15/113 (2010.01)

(52) U.S. Cl.
CPC .......... *A61K 31/713* (2013.01); *C12N 15/113* (2013.01); *C12N 2310/14* (2013.01)

(58) Field of Classification Search
CPC ..................... C12N 15/113; C12N 2310/14
See application file for complete search history.

(56) References Cited

PUBLICATIONS

H.-J. Kim et al, "Heterogeneous lengths of copy number mutations in human coagulopathy revealed by genome-wide high-density SNP array", Haematologica, The Hematology Journal: Official Organ of the European Hematology Association,vol. 97, No. 2, Feb. 1, 2012 (Feb. 1, 2012), p. 304-309.
Zhang Yang et al, "A novelPROS1mutation, c.74dupA, was identified in a protein S deficiency family", Thrombosis Research, vol. 148, Nov. 6, 2016 (Nov. 6, 2016), p. 125-127.
Sylvain Fraineau et al, "The vitamin K-dependent anticoagulant factor, protein S, inhibits multiple VEGF-A-induced angiogenesis events in a Mer-and SHP2-dependent manner", DOI: 10.1182/blood-2012-05-external link Dec. 13, 2012 (Dec. 13, 2012),Retrieved from the Internet: URL:ww.bloodjournal.org/content/bloodjournal/120/25/5073.full.pdf&usg=AOvVawOMVHZUip0nrkre3782sAXV (12 pages).
Mohd Firdaus Che Mat et al, "Silencing of PROS1 induces apoptosis and inhibits migration and invasion of glioblastoma multiforme cells", International Journal of Oncology,vol. 49, No. 6, Nov. 3, 2016 (Nov. 3, 2016), p. 2359-2366.
Bologna et al. "Blocking Protein S improves Hemostasis in Hemophilia a and b," Abstract from 58th ASH Annual Meeting, published in Blood, vol. 128, Issue 22, Dec. 2, 2016 (2 pages).
Bologna et al. "Blocking Protein S to treat Hemophilia A," Abstract from 55th ASH Annual Meeting, published in Blood vol. 122, Issue 21 Nov. 15, 2013 (3 pages).
Calzavarin et al., "Targeting anticoagulant protein S to achieve hemostasis in hemophilia," Abstracts of the 61st Annual Meeting of the Society of Thrombosis and Hemostasis Research Feb. 15-18, 2017, Basel, Switzerland (1 page), available at https://www.gth2017.net/en/Call_for_abstract.html.
Database: GenBank, [online], Accession No. NM_000313.3, *Homo sapiens* protein S (PROS1), transcript variant 2, mRNA, Oct. 3, 2017 uploaded , Internet, [retrieved on Apr. 7, 2022] <URL: https://www.ncbi.nlm.nih.gov/nuccore/223671900?sat=46&satkey=117780271>.

*Primary Examiner* — Amy H Bowman
(74) *Attorney, Agent, or Firm* — Marshall, Gerstein & Borun LLP

(57) ABSTRACT

The invention provides an siRNA against protein S for use in a method of treatment of hemophilia. Also within the scope of the present invention is a method for treating hemophilia in a patient in need thereof, comprising administering to the patient a molecule comprising a siRNA according to the invention, and a dosage form for the prevention or treatment of hemophilia, comprising a molecule comprising a siRNA according to the invention.

22 Claims, 17 Drawing Sheets
Specification includes a Sequence Listing.

Fig. 1
A
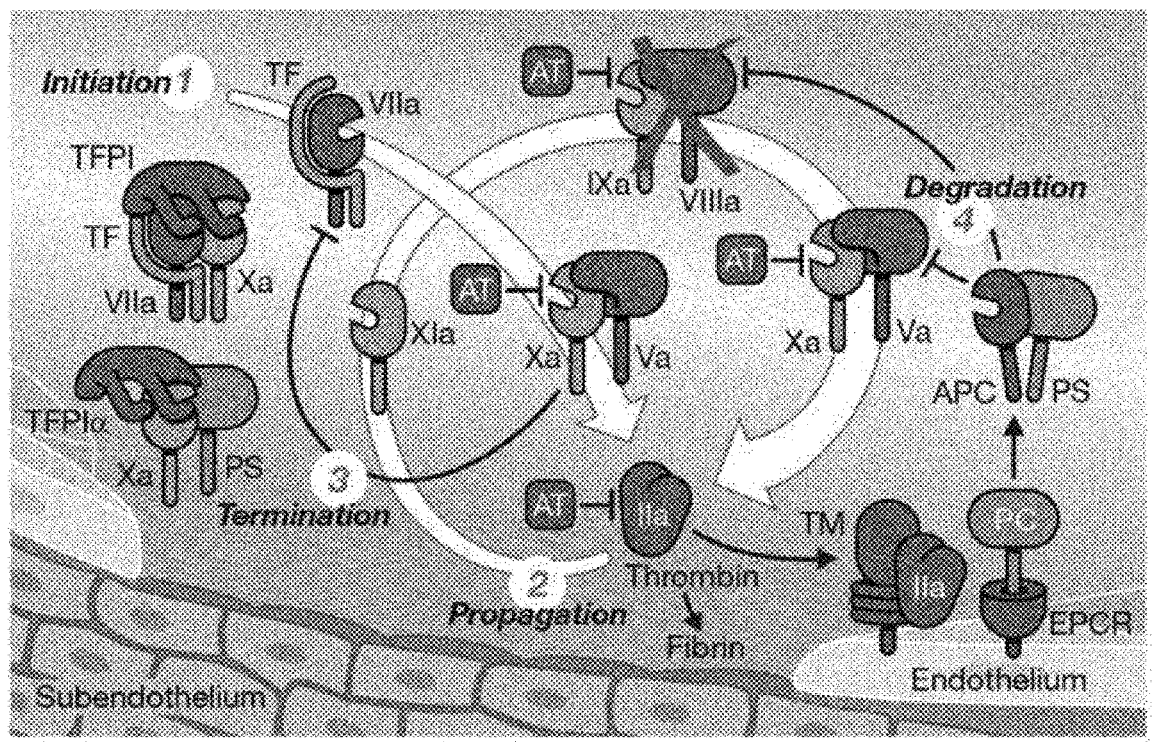
B
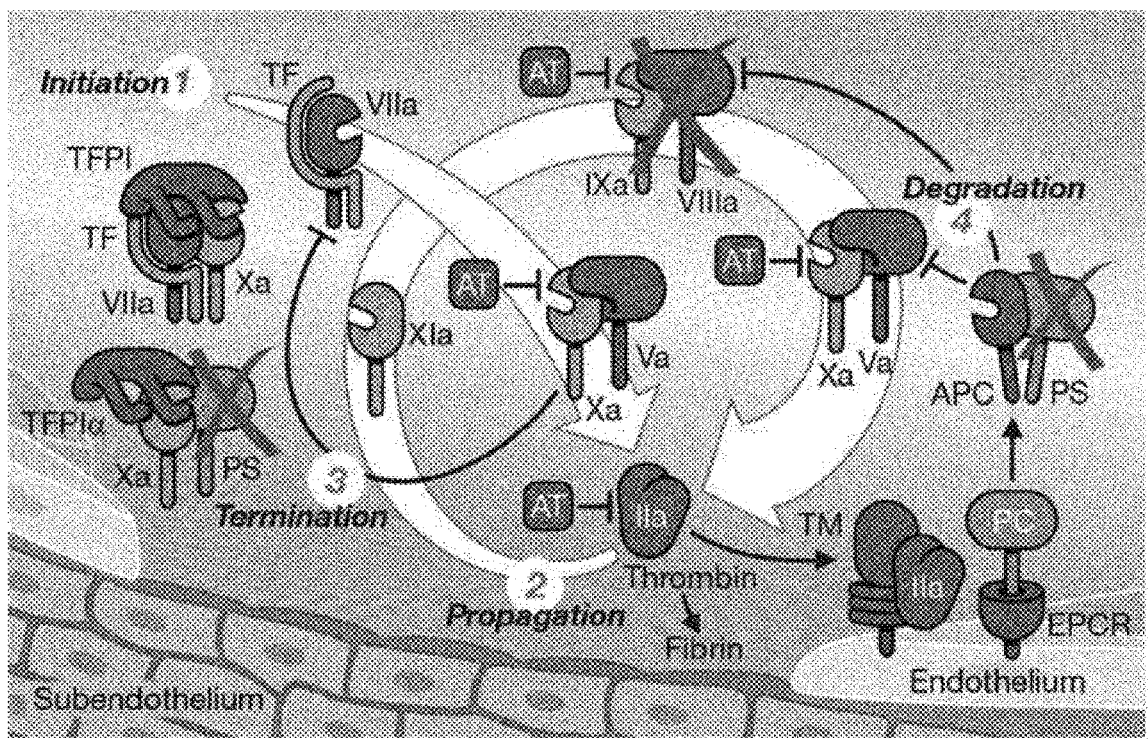

Fig.3
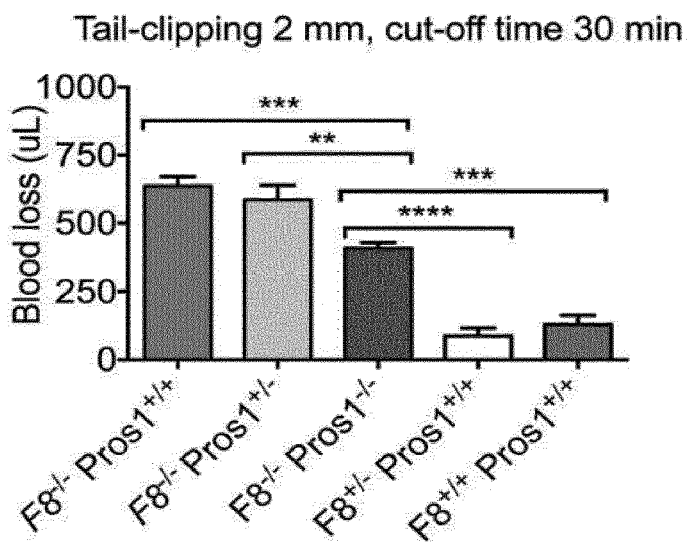
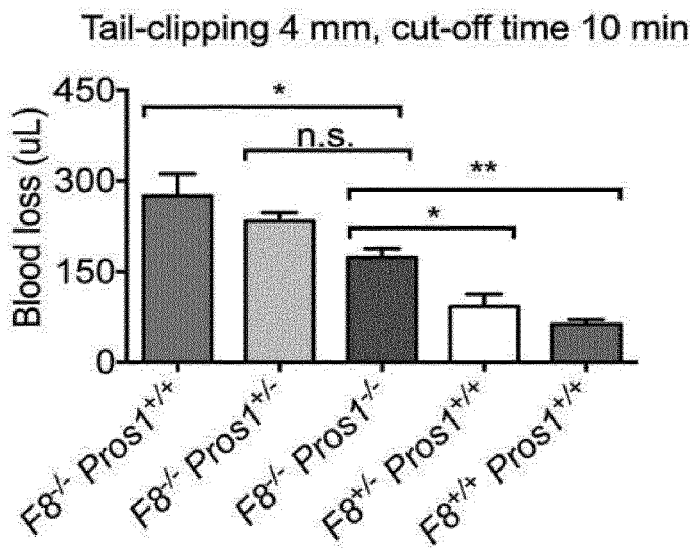
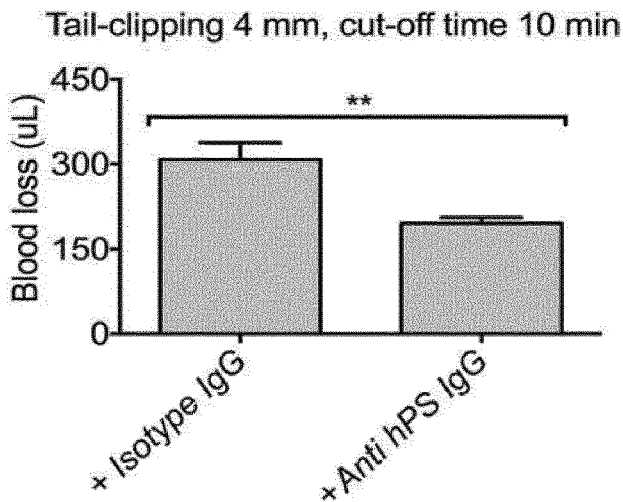

Fig.5
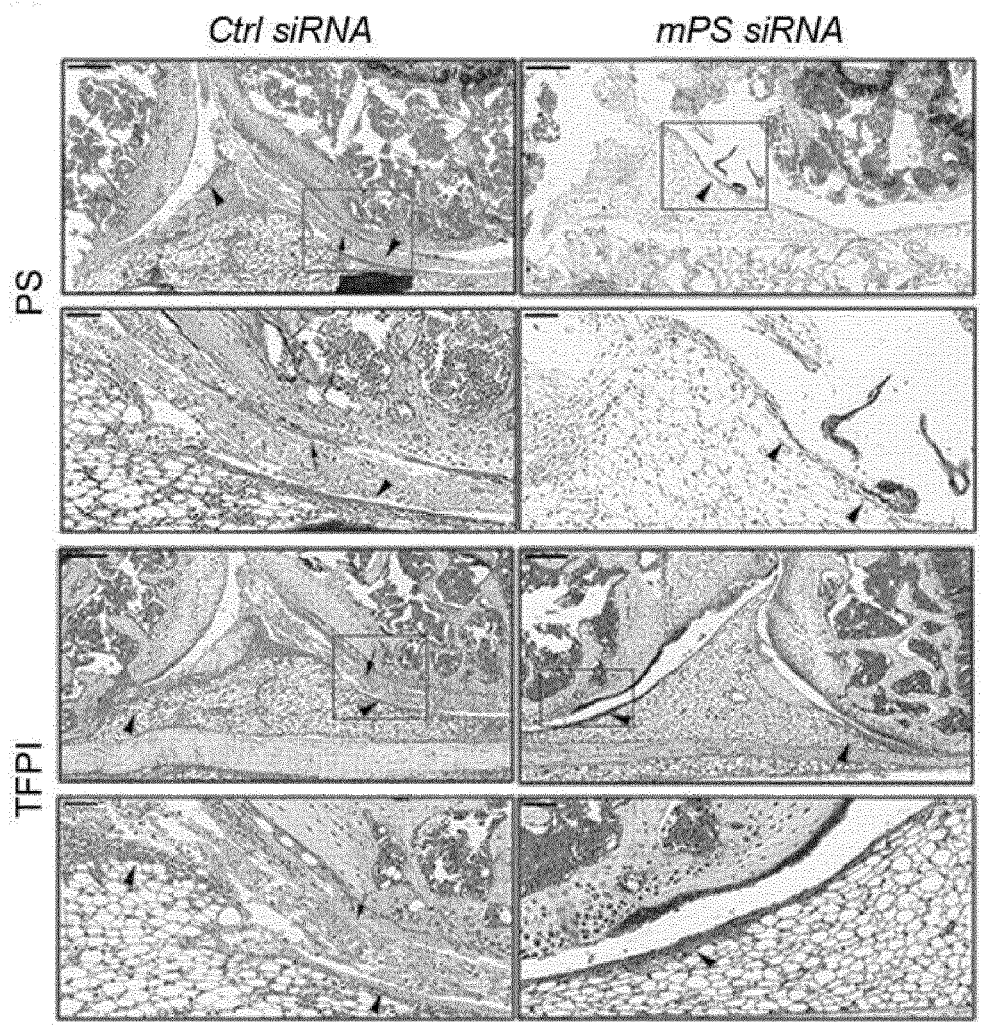
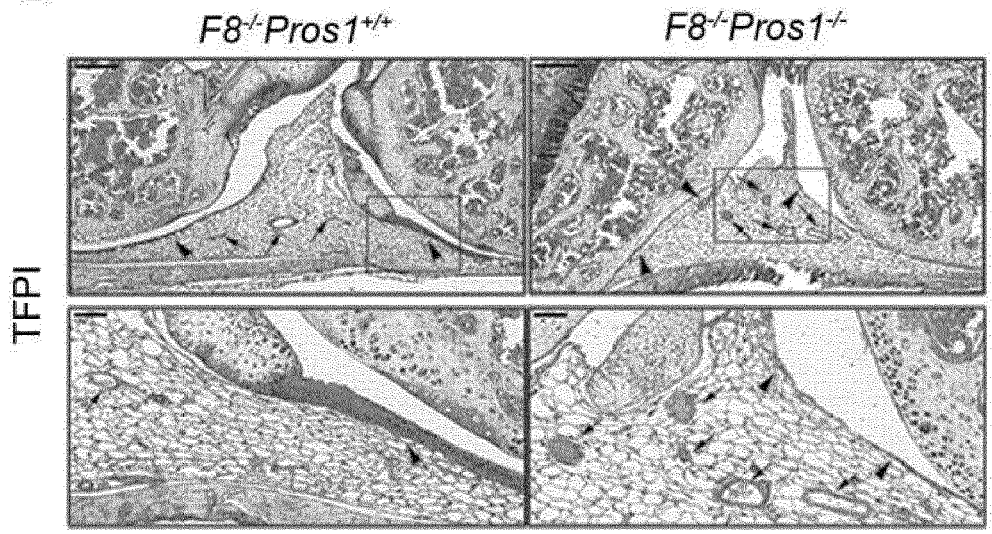

Fig.5 (continued)
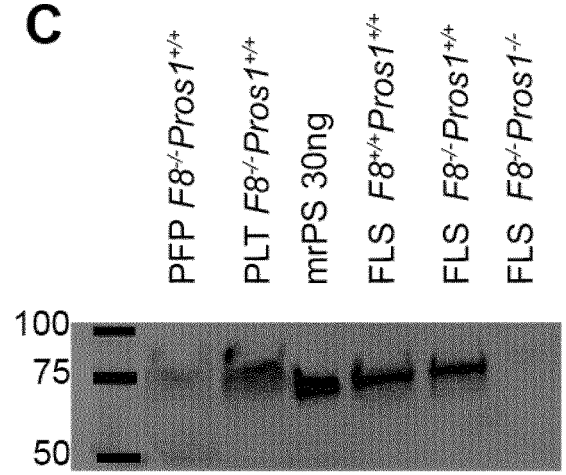
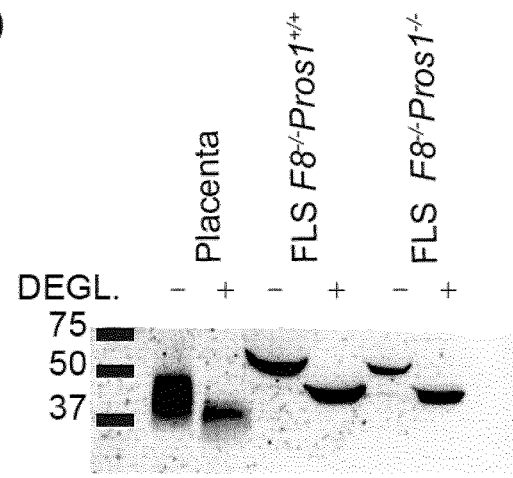
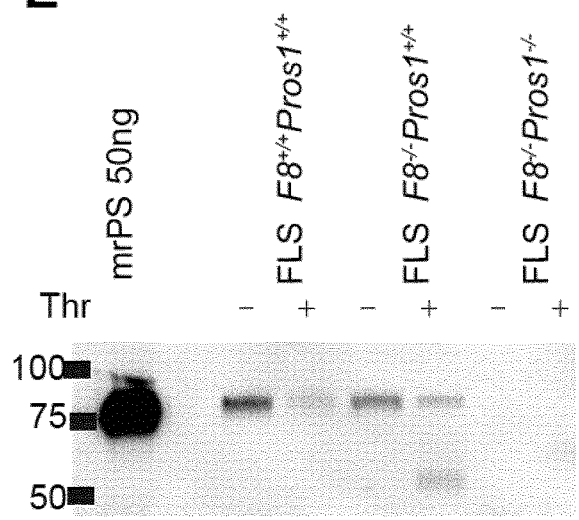
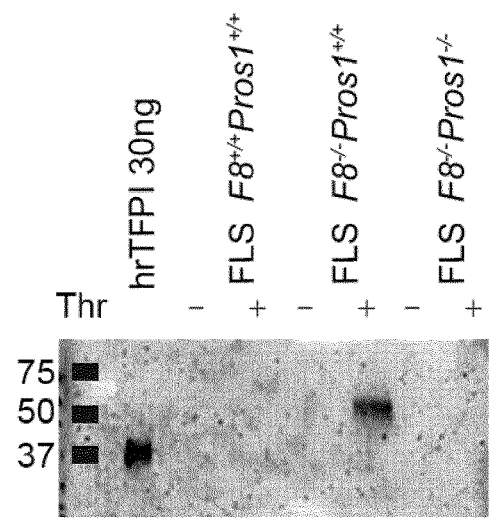

Fig. 6 (continued)
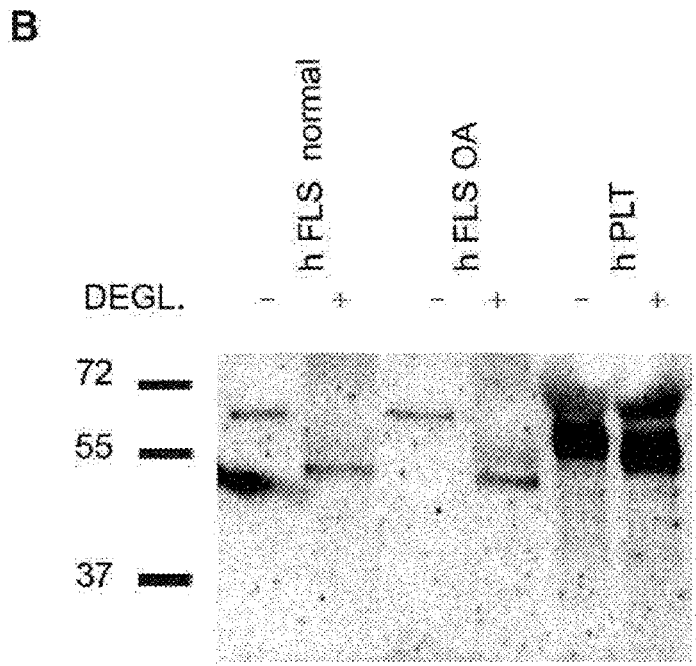
Fig.7
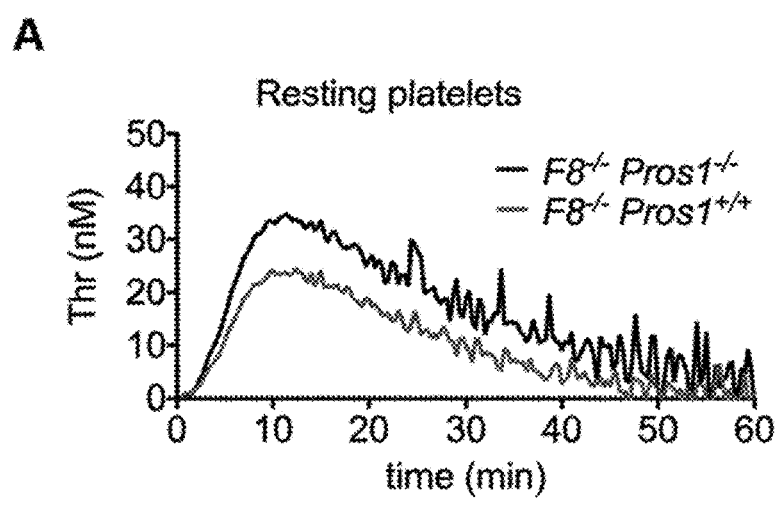
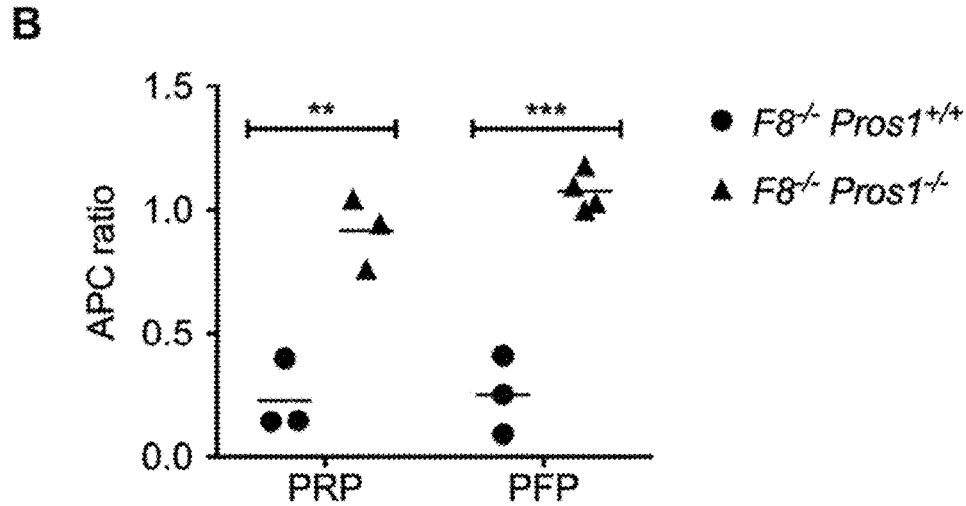

SEQUENCE LISTING

```
<160> NUMBER OF SEQ ID NOS: 68

<210> SEQ ID NO 1
<211> LENGTH: 3595
<212> TYPE: DNA
<213> ORGANISM: Homo sapiens

<400> SEQUENCE: 1
tttggaaacg tcacactgtg gaggaaaagc agcaactagg gagctggtga agaaggatgt      60
ctcagcagtg tttactaggc ctccaacact agagcccatc ccccagctcc gaaaagcttc     120
ctggaaatgt ccttgttatc acttccctc tcgggctggg cgctgggagc gggcggtctc     180
ctccgccccc ggctgttccg ccgaggctcg ctgggtcgct ggcgccgccg cgcagcacgg     240
ctcagaccga ggcgcacagg ctcgcagctc cgcggcgcct agcgctccgg tccccgccgc     300
gacgcgccac cgtccctgcc ggcgcctccg cgcgcttcga aatgagggtc ctgggtgggc     360
gctgcggggc gctgctggcg tgtctcctcc tagtgcttcc cgtctcagag gcaaacttt     420
```

| | |
|---|---|
| tgtcaaagca acaggcttca caagtcctgg ttaggaagcg tcgtgcaaat tctttacttg | 480 |
| aagaaaccaa acagggtaat cttgaaagag aatgcatcga agaactgtgc aataaagaag | 540 |
| aagccaggga ggtctttgaa aatgacccgg aaacggatta ttttatcca aaatacttag | 600 |
| tttgtcttcg ctcttttcaa actgggttat tcactgctgc acgtcagtca actaatgctt | 660 |
| atcctgacct aagaagctgt gtcaatgcca ttccagacca gtgtagtcct ctgccatgca | 720 |
| atgaagatgg atatatgagc tgcaaagatg gaaaagcttc ttttacttgc acttgtaaac | 780 |
| caggttggca aggagaaaag tgtgaatttg acataaatga atgcaaagat ccctcaaata | 840 |
| taaatggagg ttgcagtcaa atttgtgata atacacctgg aagttaccac tgttcctgta | 900 |
| aaaatggttt tgttatgctt tcaaataaga aagattgtaa agatgtggat gaatgctctt | 960 |
| tgaagccaag catttgtggc acagctgtgt gcaagaacat cccaggagat ttgaatgtg | 1020 |
| aatgccccga aggctacaga tataatctca atcaaagtc ttgtgaagat atagatgaat | 1080 |
| gctctgagaa catgtgtgct cagctttgtg tcaattaccc tggaggttac acttgctatt | 1140 |
| gtgatgggaa gaaaggattc aaacttgccc aagatcagaa gagttgtgag gttgtttcag | 1200 |
| tgtgccttcc cttgaacctt gacacaaagt atgaattact ttacttggcg gagcagtttg | 1260 |
| caggggttgt tttatattta aaatttcgtt tgccagaaat cagcagattt tcagcagaat | 1320 |
| ttgatttccg gacatatgat tcagaaggcg tgatactgta cgcagaatct atcgatcact | 1380 |
| cagcgtggct cctgattgca cttcgtggtg gaaagattga agttcagctt aagaatgaac | 1440 |
| atacatccaa aatcacaact ggaggtgatg ttattaataa tggtctatgg aatatggtgt | 1500 |
| ctgtggaaga attagaacat agtattagca ttaaaatagc taaagaagct gtgatggata | 1560 |
| taaataaacc tggaccccct tttaagccgg aaaatggatt gctggaaacc aaagtatact | 1620 |
| ttgcaggatt ccctcggaaa gtggaaagtg aactcattaa accgattaac cctcgtctag | 1680 |
| atggatgtat acgaagctgg aatttgatga agcaaggagc ttctggaata aaggaaatta | 1740 |
| ttcaagaaaa acaaaataag cattgcctgg ttactgtgga aagggctcc tactatcctg | 1800 |
| gttctggaat tgctcaattt cacatagatt ataataatgt atccagtgct gagggttggc | 1860 |
| atgtaaatgt gaccttgaat attcgtccat ccacgggcac tggtgttatg cttgccttgg | 1920 |
| tttctggtaa caacacagtg ccctttgctg tgtccttggt ggactccacc tctgaaaaat | 1980 |
| cacaggatat tctgttatct gttgaaaata ctgtaatata tcggatacag gccctaagtc | 2040 |
| tatgttccga tcaacaatct catctggaat ttagagtcaa cagaaacaat ctggagttgt | 2100 |
| cgacaccact aaaatagaa accatctccc atgaagacct tcaaagacaa cttgccgtct | 2160 |
| tggacaaagc aatgaaagca aaagtggcca catacctggg tggccttcca gatgttccat | 2220 |
| tcagtgccac accagtgaat gccttttata atggctgcat ggaagtgaat attaatggtg | 2280 |
| tacagttgga tctggatgaa gccatttcta acataatga tattagagct cactcatgtc | 2340 |
| catcagtttg gaaaagaca aagaattctt aaggcatctt ttctctgctt ataatacctt | 2400 |
| ttccttgtgt gtaattatac ttatgtttca ataacagctg aagggttta tttacaatgt | 2460 |
| gcagtctttg attattttgt ggtccttttcc tgggattttt aaaaggtcct tgtcaagga | 2520 |
| aaaaaattct gttgtgatat aaatcacagt aaagaaattc ttacttctct tgctatctaa | 2580 |
| gaatagtgaa aaataacaat tttaaatttg aattttttc ctacaaatga cagtttcaat | 2640 |
| ttttgtttgt aaaactaaat tttaatttta tcatcatgaa ctagtgtcta aatacctatg | 2700 |
| ttttttcag aaagcaagga agtaaactca aacaaagtg cgtgtaatta aatactatta | 2760 |
| atcataggca gatactattt tgtttatgtt tttgtttttt tcctgatgaa ggcagaagag | 2820 |

```
atggtggtct attaaatatg aattgaatgg agggtcctaa tgccttattt caaaacaatt    2880
cctcagggggg aacagctttg gcttcatctt tctcttgtgt ggcttcacat ttaaaccagt   2940
atctttattg aattagaaaa caagtgggac atattttcct gagagcagca caggaatctt    3000
cttcttggca gctgcagtct gtcaggatga gatatcagat taggttggat aggtggggaa    3060
atctgaagtg ggtacatttt ttaaattttg ctgtgtgggt cacacaaggt ctacattaca    3120
aaagacagaa ttcagggatg gaaaggagaa tgaacaaatg tgggagttca tagttttcct    3180
tgaatccaac ttttaattac cagagtaagt tgccaaaatg tgattgttga agtacaaaag    3240
gaactatgaa aaccagaaca aattttaaca aaaggacaac cacagaggga tatagtgaat    3300
atcgtatcat tgtaatcaaa gaagtaagga ggtaagattg ccacgtgcct gctggtactg    3360
tgatgcattt caagtggcag ttttatcacg tttgaatcta ccattcatag ccagatgtgt    3420
atcagatgtt tcactgacag ttttaacaa taaattcttt tcactgtatt ttatatcact     3480
tataataaat cggtgtataa ttttaaaatg catgtgaata tctttattat atcaactgtt    3540
tgaataaaac aaaattacat aatagacatt taactcttca aaaaaaaaaa aaaaa         3595
```

<210> SEQ ID NO 2
<211> LENGTH: 3682
<212> TYPE: DNA
<213> ORGANISM: Homo sapiens

<400> SEQUENCE: 2

```
gtcacactgt ggaggaaaag cagcaactag ggagctggtg aagaaggatg tctcagcagt      60
gtttactagg cctccaacac tagagcccat cccccagctc cgaaaagctt cctggaaatg     120
tccttgttat cacttcccct ctcgggctgg gcgctgggag cgggcggtct cctccgcccc     180
cggctgttcc gccgaggctc gctgggtcgc tggcgccgcc gcgcagcacg gctcagaccg     240
aggcgcacag gctcgcagct ccgcggcgcc tagcgctccg gtccccgccg cgacgcgcca     300
ccgtccctgc cggcgcctcc gcgcgcttcg aaatgagggt cctgggtggg cgctgcgggg    360
cgctgctggc gtgtctcctc ctagtgcttc ccgtctcaga ggcaaacttt tgtttatatt     420
ttagaaatga ttttatatac aaccgtgcat gcatttctgt attggtcggc ttatctggat    480
gcaatttttt ctattctata tgctttttgt caaagcaaca ggcttcacaa gtcctggtta    540
ggaagcgtcg tgcaaattct ttacttgaag aaaccaaaca gggtaatctt gaagagaat    600
gcatcgaaga actgtgcaat aaagaagaag ccagggaggt ctttgaaaat gacccggaaa    660
cggattattt ttatccaaaa tacttagttt gtcttcgctc ttttcaaact gggttattca    720
ctgctgcacg tcagtcaact aatgcttatc ctgacctaag aagctgtgtc aatgccattc    780
cagaccagta tagtcctctg ccatgcaatg aagatggata tatgagctgc aaagatggaa    840
aagcttcttt tacttgcact tgtaaaccag gttggcaagg agaaaagtgt gaatttgaca    900
taaatgaatg caaagatccc tcaaatataa atggaggttg cagtcaaatt tgtgataata    960
cacctggaag ttaccactgt tcctgtaaaa atggtttttgt tatgctttca aataagaaag   1020
attgtaaaga tgtggatgaa tgctctcttga agccaagcat tgtggcaca gctgtgtgca   1080
agaacatccc aggagatttt gaatgtgaat gccccgaagg ctacagatat aatctcaaat   1140
caaagtcttg tgaagatata gatgaatgct ctgagaacat gtgtgctcag ctttgtgtca   1200
attaccctgg aggttacact tgctattgtg atgggaagaa aggattcaaa cttgcccaag   1260
atcagaagag ttgtgaggtt gtttcagtgt gccttccctt gaaccttgac acaaagtatg   1320
```

-continued

```
aattacttta cttggcggag cagtttgcag gggttgtttt atatttaaaa tttcgtttgc    1380
cagaaatcag cagattttca gcagaatttg atttccggac atatgattca gaaggcgtga    1440
tactgtacgc agaatctatc gatcactcag cgtggctcct gattgcactt cgtggtggaa    1500
agattgaagt tcagcttaag aatgaacata catccaaaat cacaactgga ggtgatgtta    1560
ttaataatgg tctatggaat atggtgtctg tggaagaatt agaacatagt attagcatta    1620
aaatagctaa agaagctgtg atggatataa ataaacctgg acccctttt aagccggaaa     1680
atggattgct ggaaaccaaa gtatactttg caggattccc tcggaaagtg gaaagtgaac    1740
tcattaaacc gattaaccct cgtctagatg gatgtatacg aagctggaat ttgatgaagc    1800
aaggagcttc tggaataaag gaaattattc aagaaaaaca aaataagcat tgcctggtta    1860
ctgtggagaa gggctcctac tatcctggtt ctggaattgc tcaatttcac atagattata    1920
ataatgtatc cagtgctgag ggttggcatg taaatgtgac cttgaatatt cgtccatcca    1980
cgggcactgg tgttatgctt gccttggttt ctgtaacaa cacagtgccc tttgctgtgt     2040
ccttggtgga ctccacctct gaaaaatcac aggatattct gttatctgtt gaaaatactg    2100
taatatatcg gatacaggcc ctaagtctat gttccgatca acaatctcat ctggaattta    2160
gagtcaacag aaacaatctg gagttgtcga caccacttaa aatagaaacc atctcccatg    2220
aagaccttca aagacaactt gccgtcttgg acaaagcaat gaaagcaaaa gtggccacat    2280
acctgggtgg ccttccagat gttccattca gtgccacacc agtgaatgcc ttttataatg    2340
gctgcatgga agtgaatatt aatggtgtac agttggatct ggatgaagcc atttctaaac    2400
ataatgatat tagagctcac tcatgtccat cagtttggaa aaagacaaag aattcttaag    2460
gcatcttttc tctgcttata ataccttttc cttgtgtgta attatactta tgtttcaata    2520
acagctgaag ggttttattt acaatgtgca gtctttgatt attttgtggt cctttcctgg    2580
gatttttaaa aggtcctttg tcaaggaaaa aaattctgtt gtgatataaa tcacagtaaa    2640
gaaattctta cttctcttgc tatctaagaa tagtgaaaaa taacaatttt aaatttgaat    2700
ttttttccta caaatgacag tttcaatttt tgtttgtaaa actaaatttt aattttatca    2760
tcatgaacta gtgtctaaat acctatgttt ttttcagaaa gcaaggaagt aaactcaaac    2820
aaaagtgcgt gtaattaaat actattaatc ataggcagat actattttgt ttatgttttt    2880
gttttttttcc tgatgaaggc agaagagatg gtggtctatt aaatatgaat tgaatggagg    2940
gtcctaatgc cttatttcaa aacaattcct caggggaac agctttggct tcatctttct      3000
cttgtgtggc ttcacattta aaccagtatc tttattgaat tagaaaacaa gtgggacata    3060
ttttcctgag agcagcacag gaatcttctt cttggcagct gcagtctgtc aggatgagat    3120
atcagattag gttggatagg tggggaaatc tgaagtgggt acattttta aattttgctg      3180
tgtgggtcac acaaggtcta cattacaaaa gacagaattc agggatggaa aggagaatga    3240
acaaatgtgg gagttcatag ttttccttga atccaacttt taattaccag gtaagttgc      3300
caaaatgtga ttgttgaagt acaaaaggaa ctatgaaaac cagaacaaat tttaacaaaa    3360
ggacaaccac agagggatat agtgaatatc gtatcattgt aatcaaagaa gtaaggaggt    3420
aagattgcca cgtgcctgct ggtactgtga tgcatttcaa gtggcagttt tatcacgttt    3480
gaatctacca ttcatagcca gatgtgtatc agatgtttca ctgacagttt ttaacaataa    3540
attctttca ctgtatttta tatcacttat aataaatcgg tgtataattt taaaatgcat     3600
gtgaatatct ttattatatc aactgtttga ataaaacaaa attacataat agacatttaa    3660
ctcttcaaaa aaaaaaaaaa aa                                              3682
```

<210> SEQ ID NO 3
<211> LENGTH: 417
<212> TYPE: DNA
<213> ORGANISM: Homo sapiens

<400> SEQUENCE: 3

```
tttggaaacg tcacactgtg gaggaaaagc agcaactagg gagctggtga agaaggatgt      60
ctcagcagtg tttactaggc ctccaacact agagcccatc ccccagctcc gaaaagcttc     120
ctggaaatgt ccttgttatc acttcccctc tcgggctggg cgctgggagc gggcggtctc     180
ctccgccccc ggctgttccg ccgaggctcg ctgggtcgct ggcgccgccg cgcagcacgg     240
ctcagaccga ggcgcacagg ctcgcagctc cgcggcgcct agcgctccgg tccccgccgc     300
gacgcgccac cgtccctgcc ggcgcctccg cgcgcttcga aatgagggtc ctgggtgggc     360
gctgcgggc gctgctggcg tgtctcctcc tagtgcttcc cgtctcagag gcaaact       417
```

<210> SEQ ID NO 4
<211> LENGTH: 158
<212> TYPE: DNA
<213> ORGANISM: Homo sapiens

<400> SEQUENCE: 4

```
ttttgtcaaa gcaacaggct tcacaagtcc tggttaggaa gcgtcgtgca aattctttac      60
ttgaagaaac caaacagggt aatcttgaaa gagaatgcat cgaagaactg tgcaataaag     120
aagaagccag ggaggtcttt gaaaatgacc cggaaacg                             158
```

<210> SEQ ID NO 5
<211> LENGTH: 25
<212> TYPE: DNA
<213> ORGANISM: Homo sapiens

<400> SEQUENCE: 5

```
gattattttt atccaaaata cttag                                            25
```

<210> SEQ ID NO 6
<211> LENGTH: 87
<212> TYPE: DNA
<213> ORGANISM: Homo sapiens

<400> SEQUENCE: 6

```
tttgtcttcg ctcttttcaa actgggttat tcactgctgc acgtcagtca actaatgctt      60
atcctgacct aagaagctgt gtcaatg                                          87
```

<210> SEQ ID NO 7
<211> LENGTH: 123
<212> TYPE: DNA
<213> ORGANISM: Homo sapiens

<400> SEQUENCE: 7

```
ccattccaga ccagtgtagt cctctgccat gcaatgaaga tggatatatg agctgcaaag      60
atggaaaagc ttcttttact tgcacttgta aaccaggttg gcaaggagaa aagtgtgaat     120
ttg                                                                   123
```

<210> SEQ ID NO 8
<211> LENGTH: 132
<212> TYPE: DNA
<213> ORGANISM: Homo sapiens

<400> SEQUENCE: 8
acataaatga atgcaaagat ccctcaaata taaatggagg ttgcagtcaa atttgtgata    60
atacacctgg aagttaccac tgttcctgta aaaatggttt tgttatgctt tcaaataaga   120
aagattgtaa ag                                                       132

<210> SEQ ID NO 9
<211> LENGTH: 126
<212> TYPE: DNA
<213> ORGANISM: Homo sapiens

<400> SEQUENCE: 9
atgtggatga atgctctttg aagccaagca tttgtggcac agctgtgtgc aagaacatcc    60
caggagattt tgaatgtgaa tgccccgaag gctacagata taatctcaaa tcaaagtctt   120
gtgaag                                                              126

<210> SEQ ID NO 10
<211> LENGTH: 122
<212> TYPE: DNA
<213> ORGANISM: Homo sapiens

<400> SEQUENCE: 10
atatagatga atgctctgag aacatgtgtg ctcagctttg tgtcaattac cctggaggtt    60
acacttgcta ttgtgatggg aagaaaggat tcaaacttgc ccaagatcag aagagttgtg   120
ag                                                                  122

<210> SEQ ID NO 11
<211> LENGTH: 116
<212> TYPE: DNA
<213> ORGANISM: Homo sapiens

<400> SEQUENCE: 11
gttgtttcag tgtgccttcc cttgaacctt gacacaaagt atgaattact ttacttggcg    60
gagcagtttg caggggttgt tttatattta aaatttcgtt tgccagaaat cagcag       116

<210> SEQ ID NO 12
<211> LENGTH: 190
<212> TYPE: DNA
<213> ORGANISM: Homo sapiens

<400> SEQUENCE: 12
attttcagca gaatttgatt tccggacata tgattcagaa ggcgtgatac tgtacgcaga    60
atctatcgat cactcagcgt ggctcctgat tgcacttcgt ggtggaaaga ttgaagttca   120
gcttaagaat gaacatacat ccaaaatcac aactggaggt gatgttatta ataatggtct   180
atggaatatg                                                          190

<210> SEQ ID NO 13
<211> LENGTH: 68
<212> TYPE: DNA
<213> ORGANISM: Homo sapiens

<400> SEQUENCE: 13
gtgtctgtgg aagaattaga acatagtatt agcattaaaa tagctaaaga agctgtgatg    60
gatataaa                                                            68

<210> SEQ ID NO 14
<211> LENGTH: 169

```
<212> TYPE: DNA
<213> ORGANISM: Homo sapiens

<400> SEQUENCE: 14
taaaccnctc gtctagatgg atgtatacga agctggaatt tgatgaagca aggagcttct      60
ggaataaagg aaattattca agaaaaacaa aataagcatt gcctggttac tgtggagaag    120
ggctcctact atcctggttc tggaattgct caatttcaca tagattata                169

<210> SEQ ID NO 15
<211> LENGTH: 152
<212> TYPE: DNA
<213> ORGANISM: Homo sapiens

<400> SEQUENCE: 15
ataatgtatc cagtgctgag ggttggcatg taaatgtgac cttgaatatt cgtccatcca      60
cgggcactgg tgttatgctt gccttggttt ctggtaacaa cacagtgccc tttgctgtgt    120
ccttggtgga ctccacctct gaaaaatcac ag                                   152

<210> SEQ ID NO 16
<211> LENGTH: 226
<212> TYPE: DNA
<213> ORGANISM: Homo sapiens

<400> SEQUENCE: 16
gatattctgt tatctgttga aaatactgta atatatcgga tacaggccct aagtctatgt      60
tccgatcaac aatctcatct ggaatttaga gtcaacagaa acaatctgga gttgtcgaca    120
ccacttaaaa tagaaaccat ctcccatgaa gaccttcaaa gacaacttgc cgtcttggac    180
aaagcaatga agcaaaagt ggccacatac ctgggtggcc ttccag                    226

<210> SEQ ID NO 17
<211> LENGTH: 1384
<212> TYPE: DNA
<213> ORGANISM: Homo sapiens

<400> SEQUENCE: 17
atgttccatt cagtgccaca ccagtgaatg cctttataa tggctgcatg gaagtgaata      60
ttaatggtgt acagttggat ctggatgaag ccatttctaa acataatgat attagagctc    120
actcatgtcc atcagtttgg aaaaagacaa agaattctta aggcatcttt tctctgctta    180
taataccttt tccttgtgtg taattatact tatgtttcaa taacagctga agggttttat    240
ttacaatgtg cagtctttga ttattttgtg gtcctttcct gggattttta aaaggtcctt    300
tgtcaaggaa aaaaattctg ttgtgatata aatcacagta agaaattct tacttctctt     360 gctatctaag aatagtgaaa ataacaatt ttaaattga attttttcc tacaaatgac        420 agtttcaatt tttgtttgta aaactaaatt ttaattttat catcatgaac tagtgtctaa    480
atacctatgt ttttttcaga aagcaaggaa gtaaactcaa acaaaagtgc gtgtaattaa    540
atactattaa tcataggcag atactatttt gtttatgttt ttgtttttt cctgatgaag     600 gcagaagaga tggtggtcta ttaaatatga attgaatgga gggtcctaat gccttatttc    660
aaaacaattc ctcaggggga acagcttggg cttcatcttt ctcttgtgtg gcttcacatt    720
taaaccagta tctttattga attagaaaac aagtgggaca tattttcctg agagcagcac    780
aggaatcttc ttcttggcag ctgcagtctg tcaggatgag atatcagatt aggttggata    840
ggtggggaaa tctgaagtgg gtacattttt taaattttgc tgtgtgggtc acacaaggtc    900
```

```
tacattacaa aagacagaat tcagggatgg aaaggagaat gaacaaatgt gggagttcat    960
agttttcctt gaatccaact tttaattacc agagtaagtt gccaaaatgt gattgttgaa   1020
gtacaaaagg aactatgaaa accagaacaa atttaacaa aaggacaacc acagagggat   1080
atagtgaata tcgtatcatt gtaatcaaag aagtaaggag gtaagattgc cacgtgcctg   1140
ctggtactgt gatgcatttc aagtggcagt tttatcacgt ttgaatctac cattcatagc   1200
cagatgtgta tcagatgttt cactgacagt ttttaacaat aaattctttt cactgtattt   1260
tatatcactt ataataaatc ggtgtataat tttaaaatgc atgtgaatat ctttattata   1320
tcaactgttt gaataaaaca aaattacata atagacattt aactcttcaa aaaaaaaaa   1380 aaaa                                                                1384

<210> SEQ ID NO 18
<211> LENGTH: 96
<212> TYPE: DNA
<213> ORGANISM: Homo sapiens

<400> SEQUENCE: 18
tttgtttata ttttagaaat gattttatat acaaccgtgc atgcatttct gtattggtcg     60
gcttatctgg atgcaattt ttctattcta tatgct                                96

<210> SEQ ID NO 19
<211> LENGTH: 19
<212> TYPE: RNA
<213> ORGANISM: Homo sapiens

<400> SEQUENCE: 19
uauuccagaa gcuccuugc                                                  19

<210> SEQ ID NO 20
<211> LENGTH: 19
<212> TYPE: RNA
<213> ORGANISM: Homo sapiens

<400> SEQUENCE: 20
uuugugucaa gguucaagg                                                  19

<210> SEQ ID NO 21
<211> LENGTH: 19
<212> TYPE: RNA
<213> ORGANISM: Homo sapiens

<400> SEQUENCE: 21
auugacacag cuucuuagg                                                  19

<210> SEQ ID NO 22
<211> LENGTH: 19
<212> TYPE: RNA
<213> ORGANISM: Homo sapiens

<400> SEQUENCE: 22
uauaucugua gccuucggg                                                  19

<210> SEQ ID NO 23
<211> LENGTH: 19
<212> TYPE: RNA
<213> ORGANISM: Homo sapiens

<400> SEQUENCE: 23
aaccucacaa cucuucuga                                                  19
```

```
<210> SEQ ID NO 24
<211> LENGTH: 19
<212> TYPE: RNA
<213> ORGANISM: Homo sapiens

<400> SEQUENCE: 24
uccaucacag cuucuuuag                                               19

<210> SEQ ID NO 25
<211> LENGTH: 19
<212> TYPE: RNA
<213> ORGANISM: Homo sapiens

<400> SEQUENCE: 25
auuugcacga cgcuuccua                                               19

<210> SEQ ID NO 26
<211> LENGTH: 19
<212> TYPE: RNA
<213> ORGANISM: Homo sapiens

<400> SEQUENCE: 26
uugcacaguu cuucgaugc                                               19

<210> SEQ ID NO 27
<211> LENGTH: 19
<212> TYPE: RNA
<213> ORGANISM: Homo sapiens

<400> SEQUENCE: 27
uauguggcca cuuuugcuu                                               19

<210> SEQ ID NO 28
<211> LENGTH: 19
<212> TYPE: RNA
<213> ORGANISM: Homo sapiens

<400> SEQUENCE: 28
uuuucaaaga ccucccugg                                               19

<210> SEQ ID NO 29
<211> LENGTH: 19
<212> TYPE: RNA
<213> ORGANISM: Homo sapiens

<400> SEQUENCE: 29
uuccacagac accauauuc                                               19

<210> SEQ ID NO 30
<211> LENGTH: 19
<212> TYPE: RNA
<213> ORGANISM: Homo sapiens

<400> SEQUENCE: 30
auauucacuu ccaugcagc                                               19

<210> SEQ ID NO 31
<211> LENGTH: 19
<212> TYPE: RNA
<213> ORGANISM: Homo sapiens

<400> SEQUENCE: 31
```
aagcugagca cacauguuc                                                  19

<210> SEQ ID NO 32
<211> LENGTH: 19
<212> TYPE: RNA
<213> ORGANISM: Homo sapiens

<400> SEQUENCE: 32
uugacugcaa ccuccauuu                                                  19

<210> SEQ ID NO 33
<211> LENGTH: 19
<212> TYPE: RNA
<213> ORGANISM: Homo sapiens

<400> SEQUENCE: 33
uucugcugaa aaucugcug                                                  19

<210> SEQ ID NO 34
<211> LENGTH: 19
<212> TYPE: RNA
<213> ORGANISM: Homo sapiens

<400> SEQUENCE: 34
aaucuuucca ccacgaagu                                                  19

<210> SEQ ID NO 35
<211> LENGTH: 19
<212> TYPE: RNA
<213> ORGANISM: Homo sapiens

<400> SEQUENCE: 35
uugguuucca gcaauccau                                                  19

<210> SEQ ID NO 36
<211> LENGTH: 19
<212> TYPE: RNA
<213> ORGANISM: Homo sapiens

<400> SEQUENCE: 36
uagacuuagg gccuguauc                                                  19

<210> SEQ ID NO 37
<211> LENGTH: 19
<212> TYPE: RNA
<213> ORGANISM: Homo sapiens

<400> SEQUENCE: 37
cuuugcagcu cauauaucc                                                  19

<210> SEQ ID NO 38
<211> LENGTH: 19
<212> TYPE: RNA
<213> ORGANISM: Homo sapiens

<400> SEQUENCE: 38
ugcuuucauu gcuuugucc                                                  19

<210> SEQ ID NO 39
<211> LENGTH: 19
<212> TYPE: RNA
<213> ORGANISM: Homo sapiens

<400> SEQUENCE: 39
ucacuuucca cuuuccgag    19

<210> SEQ ID NO 40
<211> LENGTH: 19
<212> TYPE: RNA
<213> ORGANISM: Homo sapiens

<400> SEQUENCE: 40
uuugacugca accuccauu    19

<210> SEQ ID NO 41
<211> LENGTH: 19
<212> TYPE: RNA
<213> ORGANISM: Homo sapiens

<400> SEQUENCE: 41
aucuccuggg auguucuug    19

<210> SEQ ID NO 42
<211> LENGTH: 19
<212> TYPE: RNA
<213> ORGANISM: Homo sapiens

<400> SEQUENCE: 42
aauagcaagu guaaccucc    19

<210> SEQ ID NO 43
<211> LENGTH: 19
<212> TYPE: RNA
<213> ORGANISM: Homo sapiens

<400> SEQUENCE: 43
uaucacgccu ucugaauca    19

<210> SEQ ID NO 44
<211> LENGTH: 19
<212> TYPE: RNA
<213> ORGANISM: Homo sapiens

<400> SEQUENCE: 44
ugcuucauca aauuccagc    19

<210> SEQ ID NO 45
<211> LENGTH: 19
<212> TYPE: RNA
<213> ORGANISM: Homo sapiens

<400> SEQUENCE: 45
uuauuccaga agcuccuug    19

<210> SEQ ID NO 46
<211> LENGTH: 19
<212> TYPE: RNA
<213> ORGANISM: Homo sapiens

<400> SEQUENCE: 46
uguucucaga gcauucauc    19

<210> SEQ ID NO 47
<211> LENGTH: 19
<212> TYPE: RNA
<213> ORGANISM: Homo sapiens

```
<400> SEQUENCE: 47
uaaccuccag gguaauuga                                           19

<210> SEQ ID NO 48
<211> LENGTH: 19
<212> TYPE: RNA
<213> ORGANISM: Homo sapiens

<400> SEQUENCE: 48
aauccuuucu ucccaucac                                           19

<210> SEQ ID NO 49
<211> LENGTH: 19
<212> TYPE: RNA
<213> ORGANISM: Homo sapiens

<400> SEQUENCE: 49
aacucuucug aucuugggc                                           19

<210> SEQ ID NO 50
<211> LENGTH: 19
<212> TYPE: RNA
<213> ORGANISM: Homo sapiens

<400> SEQUENCE: 50
uucacuuucc acuuccga                                            19

<210> SEQ ID NO 51
<211> LENGTH: 19
<212> TYPE: RNA
<213> ORGANISM: Homo sapiens

<400> SEQUENCE: 51
aaaaucuccu gggauguuc                                           19

<210> SEQ ID NO 52
<211> LENGTH: 19
<212> TYPE: RNA
<213> ORGANISM: Homo sapiens

<400> SEQUENCE: 52
guucucagag cauucaucu                                           19

<210> SEQ ID NO 53
<211> LENGTH: 19
<212> TYPE: RNA
<213> ORGANISM: Homo sapiens

<400> SEQUENCE: 53
auccuuucuu cccaucaca                                           19

<210> SEQ ID NO 54
<211> LENGTH: 19
<212> TYPE: RNA
<213> ORGANISM: Homo sapiens

<400> SEQUENCE: 54
aguaucacgc cuucugaau                                           19

<210> SEQ ID NO 55
<211> LENGTH: 19
<212> TYPE: RNA
<213> ORGANISM: Homo sapiens
```

```
<400> SEQUENCE: 55
acaccauauu ccauagacc                                            19

<210> SEQ ID NO 56
<211> LENGTH: 19
<212> TYPE: RNA
<213> ORGANISM: Homo sapiens

<400> SEQUENCE: 56
uccacagaca ccauauucc                                            19

<210> SEQ ID NO 57
<211> LENGTH: 19
<212> TYPE: RNA
<213> ORGANISM: Homo sapiens

<400> SEQUENCE: 57
ucuuccacag acaccauau                                            19

<210> SEQ ID NO 58
<211> LENGTH: 19
<212> TYPE: RNA
<213> ORGANISM: Homo sapiens

<400> SEQUENCE: 58
uaauucuucc acagacacc                                            19

<210> SEQ ID NO 59
<211> LENGTH: 19
<212> TYPE: RNA
<213> ORGANISM: Homo sapiens

<400> SEQUENCE: 59
guucacuuuc cacuuuccg                                            19

<210> SEQ ID NO 60
<211> LENGTH: 19
<212> TYPE: RNA
<213> ORGANISM: Homo sapiens

<400> SEQUENCE: 60
aauuccagaa ccaggauag                                            19

<210> SEQ ID NO 61
<211> LENGTH: 19
<212> TYPE: RNA
<213> ORGANISM: Homo sapiens

<400> SEQUENCE: 61
aagggcacug uguuguuac                                            19

<210> SEQ ID NO 62
<211> LENGTH: 19
<212> TYPE: RNA
<213> ORGANISM: Homo sapiens

<400> SEQUENCE: 62
cuggcuucuu cuuuauugc                                            19

<210> SEQ ID NO 63
<211> LENGTH: 19
<212> TYPE: RNA
```

```
<213> ORGANISM: Homo sapiens

<400> SEQUENCE: 63
ucccuggcuu cuucuuuau                                              19

<210> SEQ ID NO 64
<211> LENGTH: 19
<212> TYPE: RNA
<213> ORGANISM: Homo sapiens

<400> SEQUENCE: 64
uuuccaucuu ugcagcuca                                              19

<210> SEQ ID NO 65
<211> LENGTH: 19
<212> TYPE: RNA
<213> ORGANISM: Homo sapiens

<400> SEQUENCE: 65
agcuuuucca ucuuugcag                                              19

<210> SEQ ID NO 66
<211> LENGTH: 19
<212> TYPE: RNA
<213> ORGANISM: Homo sapiens

<400> SEQUENCE: 66
uucugcguac aguaucacg                                              19

<210> SEQ ID NO 67
<211> LENGTH: 19
<212> TYPE: RNA
<213> ORGANISM: Homo sapiens

<400> SEQUENCE: 67
auaacaucac cuccaguug                                              19

<210> SEQ ID NO 68
<211> LENGTH: 19
<212> TYPE: RNA
<213> ORGANISM: Homo sapiens

<400> SEQUENCE: 68
guauacuuug guuuccagc                                              19
```

USE OF SPECIFIC SIRNA AGAINST PROTEIN S FOR THE TREATMENT OF HEMOPHILIA

CROSS-REFERENCE TO RELATED APPLICATIONS

This is the U.S. National Stage of International Patent Application No. PCT/EP2017/078107 filed on Nov. 2, 2017, which in turn claims the benefit of International Patent Application No. PCT/EP2017/077986 filed on Nov. 1, 2017.

The present invention relates to a treatment of hemophilia using siRNA directed against protein S.

INCORPORATION BY REFERENCE OF MATERIAL SUBMITTED ELECTRONICALLY

The Sequence Listing, which is a part of the present disclosure, is submitted concurrently as a text file. The name of the text file containing the Sequence Listing is "55882_Seqlisting.txt", which was created on Jul. 27, 2021, and is 23,869 bytes in size. The subject matter of the Sequence Listing is incorporated herein in its entirety by reference.

BACKGROUND OF THE INVENTION

Hemophilia A (HA) and B (HB) are hereditary X-linked disorders. They are caused by mutations in factor VIII (FVIII) (F8) or factor IX (FIX) gene (F9), respectively, leading to the deficiency of the encoded protein that is an essential component of the intrinsic pathway of coagulation (FIG. 1A).

Patients with severe hemophilia often suffer from spontaneous bleeding within the musculoskeletal system, such as hemarthrosis. This can result in disability at a young age if left untreated.

Current hemophilia treatment involves factor replacement therapy. This therapy improves quality of life (QoL) but some drawbacks remain. Factors are administered intravenously and, because of their short half-life, they must be repetitively infused, a practice carrying a major discomfort for the patient and a risk for infection and venous damage. More importantly, patients under factor replacement therapy can develop inhibitory alloantibodies. Inhibitors render replacement therapy ineffective, limit patient access to a safe and effective standard of care and predispose them to an increased morbidity and mortality risk.

New therapies focus on the development of products capable of decreasing the frequency of prophylactic infusions, thus potentially improving both compliance to therapy and QoL. Besides long-lasting FVIII and FIX, novel approaches comprise the replacement of the gene necessary for production of endogenous coagulation factor, the bispecific antibody technology to mimic the coagulation function of the missing factor, and the targeting of coagulation inhibitors such as tissue factor pathway inhibitor (TFPI) or antithrombin as a strategy to rebalance coagulation in patients with hemophilia. Recently, it was shown that an activated protein C (APC)-specific serpin rescues thrombin generation in vitro and restores hemostasis in hemophilia mouse models.

Based on the above mentioned state of the art, the objective of the present invention is to provide means and methods to provide a novel treatment for hemophilia. This objective is attained by the claims of the present specification.

DESCRIPTION OF THE INVENTION

A first aspect of the invention provides a siRNA against protein S for use in a method of treatment of hemophilia.

The term hemophilia in the context of the present specification relates to a condition in which the body's ability to make blood clots is impaired. Genetic forms of hemophilia includes the genetic disorders hemophilia A, hemophilia B and hemophilia C.

Protein S in the context of the present specification relates to human "Vitamin K-dependent protein S" (UniProt ID P07225), encoded by the gene PROS1 (NCBI Gene ID: 5627).

Two transcript variants of human protein S exist. Transcript variant 2 lacks an alternate in-frame exon in the 5' coding region compared to transcript variant 1. The encoded isoform 2 is shorter than isoform 1. Transcript variant 2 is characterized by SEQ ID NO 001. Transcript variant 1 is characterized by SEQ ID NO 002.

The term siRNA (small/short interfering RNA) in the context of the present specification relates to a RNA molecule capable of interfering with the expression (in other words: preventing the expression) of a gene comprising a nucleic acid sequence complementary to the sequence of the siRNA in a process called RNA interference. The term siRNA is meant to encompass both single stranded siRNA and double stranded siRNA. siRNA is usually characterized by a length of 17-24 bp. Double stranded siRNA is derived from l longer double stranded RNA molecules (dsRNA). The long dsRNA is cleaved by an endo-ribonuclease (called Dicer) to form double stranded siRNA. In a nucleoprotein complex (called RISC), the double stranded siRNA is unwound to form single stranded siRNA. RNA interference often works via binding of an siRNA molecule to the an mRNA molecule having a complementary sequence, resulting in degradation of the mRNA. RNA interference is also possible by binding of an siRNA molecule to an intronic sequence of a pre-mRNA (an immature, non-spliced mRNA) within the nucleus of a cell, resulting in degradation of the pre-mRNA.

The inventors investigated whether targeting protein S (PS) can promote hemostasis in hemophilia by re-balancing coagulation (FIG. 1B). PS, encoded by the PROS1 gene, acts as cofactor for APC in the inactivation of factor Va (FVa) and FVIIIa, and for TFPI in the inhibition of FXa. This dual role makes PS a key regulator of thrombin generation.

In certain embodiments, the siRNA comprises 17-24 nucleotides.

In certain embodiments, the siRNA comprises 18-22 nucleotides.

In certain embodiments, the siRNA comprises 19 nucleotides.

In certain embodiments, the siRNA is characterized by a sequence reverse complementary to SEQ ID 001.

In certain embodiments, the siRNA is characterized by a sequence reverse complementary to SEQ ID 002.

In certain embodiments, the is characterized by a sequence reverse complementary to a sequence selected from the group comprising SEQ ID NO 003, SEQ ID NO 004, SEQ ID NO 005, SEQ ID NO 006, SEQ ID NO 007, SEQ ID NO 008, SEQ ID NO 009, SEQ ID NO 010, SEQ ID NO 011, SEQ ID NO 012, SEQ ID NO 013, SEQ ID NO 014, SEQ ID NO 015, SEQ ID NO 016, SEQ ID NO 017 and SEQ ID NO 018.

In certain embodiments, the siRNA is characterized by a sequence reverse complementary to SEQ ID NO 003.

In certain embodiments, the siRNA is characterized by a sequence reverse complementary to SEQ ID NO 004.

In certain embodiments, the siRNA is characterized by a sequence reverse complementary to SEQ ID NO 005.

In certain embodiments, the siRNA is characterized by a sequence reverse complementary to SEQ ID NO 006.

In certain embodiments, the siRNA is characterized by a sequence reverse complementary to SEQ ID NO 007.

In certain embodiments, the siRNA is characterized by a sequence reverse complementary to SEQ ID NO 008.

In certain embodiments, the siRNA is characterized by a sequence reverse complementary to SEQ ID NO 009.

In certain embodiments, the siRNA is characterized by a sequence reverse complementary to SEQ ID NO 010.

In certain embodiments, the siRNA is characterized by a sequence reverse complementary to SEQ ID NO 011.

In certain embodiments, the siRNA is characterized by a sequence reverse complementary to SEQ ID NO 012.

In certain embodiments, the siRNA is characterized by a sequence reverse complementary to SEQ ID NO 013.

In certain embodiments, the siRNA is characterized by a sequence reverse complementary to SEQ ID NO 014.

In certain embodiments, the siRNA is characterized by a sequence reverse complementary to SEQ ID NO 015.

In certain embodiments, the siRNA is characterized by a sequence reverse complementary to SEQ ID NO 016.

In certain embodiments, the siRNA is characterized by a sequence reverse complementary to SEQ ID NO 017.

In certain embodiments, the siRNA is characterized by a sequence reverse complementary to SEQ ID NO 018.

In certain embodiments, the siRNA is characterized by a sequence reverse complementary to a sequence formed by juxtaposing any two consecutive sequences of the sequences defined above. By way of non-limiting example, the siRNA is characterized by a sequence reverse complementary to a sequence formed by juxtaposing SEQ ID NO 014 and SEQ ID NO 015.

In certain embodiments, the siRNA is characterized by a sequence reverse complementary to a sequence selected from the group comprising of SEQ ID NO 014 (exon 12), SEQ ID NO 011 (exon 9), SEQ ID NO 006 (exon 4), SEQ ID NO 012 (exon 10) and SEQ ID NO 013 (exon 11).

In certain embodiments, the siRNA is characterized by a sequence reverse complementary to a sequence characterized by nucleotides 1-100, 101-200, 201-300, 301-400, 301-400, 401-500, 501-600, 601-700, 701-800, 801-900, 901-1000, 1001-1100, 1101-1200, 1201-1300, 1301-1400, 1501-1600, 1701-1800, 1801-1900, 1901-2000, 2001-2100, 2101-2200, 2201-2300, 2301-2400, 2501-2600, 2701-2800, 2801-2900, 2901-3000, 3001-3100, 3101-3200, 3201-3300, 3301-3400, 3401-3500 or 3501-3580 of SEQ ID NO 001.

In certain embodiments, the siRNA is characterized by a sequence reverse complementary to a sequence characterized by nucleotides 1-100 of SEQ ID NO 001.

In certain embodiments, the siRNA is characterized by a sequence reverse complementary to a sequence characterized by nucleotides 101-200 of SEQ ID NO 001.

In certain embodiments, the siRNA is characterized by a sequence reverse complementary to a sequence characterized by nucleotides 201-300 of SEQ ID NO 001.

In certain embodiments, the siRNA is characterized by a sequence reverse complementary to a sequence characterized by nucleotides 301-400 of SEQ ID NO 001.

In certain embodiments, the siRNA is characterized by a sequence reverse complementary to a sequence characterized by nucleotides 401-500 of SEQ ID NO 001.

In certain embodiments, the siRNA is characterized by a sequence reverse complementary to a sequence characterized by nucleotides 501-600 of SEQ ID NO 001.

In certain embodiments, the siRNA is characterized by a sequence reverse complementary to a sequence characterized by nucleotides 601-700 of SEQ ID NO 001.

In certain embodiments, the siRNA is characterized by a sequence reverse complementary to a sequence characterized by nucleotides 701-800 of SEQ ID NO 001.

In certain embodiments, the siRNA is characterized by a sequence reverse complementary to a sequence characterized by nucleotides 801-900 of SEQ ID NO 001.

In certain embodiments, the siRNA is characterized by a sequence reverse complementary to a sequence characterized by nucleotides 901-1000 of SEQ ID NO 001.

In certain embodiments, the siRNA is characterized by a sequence reverse complementary to a sequence characterized by nucleotides 1001-1100 of SEQ ID NO 001.

In certain embodiments, the siRNA is characterized by a sequence reverse complementary to a sequence characterized by nucleotides 1100-1200 of SEQ ID NO 001.

In certain embodiments, the siRNA is characterized by a sequence reverse complementary to a sequence characterized by nucleotides 1201-1300 of SEQ ID NO 001.

In certain embodiments, the siRNA is characterized by a sequence reverse complementary to a sequence characterized by nucleotides 1301-1400 of SEQ ID NO 001.

In certain embodiments, the siRNA is characterized by a sequence reverse complementary to a sequence characterized by nucleotides 1401-1500 of SEQ ID NO 001.

In certain embodiments, the siRNA is characterized by a sequence reverse complementary to a sequence characterized by nucleotides 1501-1600 of SEQ ID NO 001.

In certain embodiments, the siRNA is characterized by a sequence reverse complementary to a sequence characterized by nucleotides 1601-1700 of SEQ ID NO 001.

In certain embodiments, the siRNA is characterized by a sequence reverse complementary to a sequence characterized by nucleotides 1701-1800 of SEQ ID NO 001.

In certain embodiments, the siRNA is characterized by a sequence reverse complementary to a sequence characterized by nucleotides 1801-1900 of SEQ ID NO 001.

In certain embodiments, the siRNA is characterized by a sequence reverse complementary to a sequence characterized by nucleotides 1901-2000 of SEQ ID NO 001.

In certain embodiments, the siRNA is characterized by a sequence reverse complementary to a sequence characterized by nucleotides 2001-2100 of SEQ ID NO 001.

In certain embodiments, the siRNA is characterized by a sequence reverse complementary to a sequence characterized by nucleotides 2100-2200 of SEQ ID NO 001.

In certain embodiments, the siRNA is characterized by a sequence reverse complementary to a sequence characterized by nucleotides 2201-2300 of SEQ ID NO 001.

In certain embodiments, the siRNA is characterized by a sequence reverse complementary to a sequence characterized by nucleotides 2301-2400 of SEQ ID NO 001.

In certain embodiments, the siRNA is characterized by a sequence reverse complementary to a sequence characterized by nucleotides 2401-2500 of SEQ ID NO 001.

In certain embodiments, the siRNA is characterized by a sequence reverse complementary to a sequence characterized by nucleotides 2501-2600 of SEQ ID NO 001.

In certain embodiments, the siRNA is characterized by a sequence reverse complementary to a sequence characterized by nucleotides 2601-2700 of SEQ ID NO 001.

In certain embodiments, the siRNA is characterized by a sequence reverse complementary to a sequence characterized by nucleotides 2701-2800 of SEQ ID NO 001.

In certain embodiments, the siRNA is characterized by a sequence reverse complementary to a sequence characterized by nucleotides 2801-2900 of SEQ ID NO 001.

In certain embodiments, the siRNA is characterized by a sequence reverse complementary to a sequence characterized by nucleotides 2901-3000 of SEQ ID NO 001.

In certain embodiments, the siRNA is characterized by a sequence reverse complementary to a sequence characterized by nucleotides 3001-3100 of SEQ ID NO 001.

In certain embodiments, the siRNA is characterized by a sequence reverse complementary to a sequence characterized by nucleotides 3100-3200 of SEQ ID NO 001.

In certain embodiments, the siRNA is characterized by a sequence reverse complementary to a sequence characterized by nucleotides 3201-3300 of SEQ ID NO 001.

In certain embodiments, the siRNA is characterized by a sequence reverse complementary to a sequence characterized by nucleotides 3301-3400 of SEQ ID NO 001.

In certain embodiments, the siRNA is characterized by a sequence reverse complementary to a sequence characterized by nucleotides 3401-3500 of SEQ ID NO 001.

In certain embodiments, the siRNA is characterized by a sequence reverse complementary to a sequence characterized by nucleotides 3501-3580 of SEQ ID NO 001.

In certain embodiments, the siRNA is characterized by a sequence reverse complementary to a sequence formed by juxtaposing any two consecutive sequences of the sequences defined above. By way of non-limiting example, the siRNA is characterized by a sequence reverse complementary to a sequence formed by juxtaposing 1501-1600 of SEQ ID NO 001 and 1501-1600 of SEQ ID NO 001.

In certain embodiments, the siRNA is directed against an intronic sequence of protein S.

In certain embodiments, the is characterized by a sequence reverse complementary to a sequence selected from the group comprising of SEQ ID NO 014 (exon 12), SEQ ID NO 011 (exon 9), SEQ ID NO 006 (exon 4), SEQ ID NO 012 (exon 10) and SEQ ID NO 013 (exon 11).

In certain embodiments, the siRNA is characterized by a sequence comprising or consisting of a sequence selected from the group comprising SEQ ID NO 019 (siRNA_1), SEQ ID NO 020 (siRNA_2), SEQ ID NO 021 (siRNA_3), SEQ ID NO 022 (siRNA_4), SEQ ID NO 023 (siRNA_5), SEQ ID NO 024 (siRNA_6), SEQ ID NO 025 (siRNA_7), SEQ ID NO 026 (siRNA_8), SEQ ID NO 027 (siRNA_9), SEQ ID NO 028 (siRNA 10), SEQ ID NO 029 (siRNA 11), SEQ ID NO 030 (siRNA_12), SEQ ID NO 031 (siRNA_13), SEQ ID NO 032 (siRNA_14), SEQ ID NO 033 (siRNA_15), SEQ ID NO 034 (siRNA_16), SEQ ID NO 035 (siRNA_17), SEQ ID NO 036 (siRNA_18), SEQ ID NO 037 (siRNA_19), SEQ ID NO 038 (siRNA_20), SEQ ID NO 039 (siRNA_21), SEQ ID NO 040 (siRNA_22), SEQ ID NO 041 (siRNA_23), SEQ ID NO 042 (siRNA_24), SEQ ID NO 043 (siRNA_25), SEQ ID NO 044 (siRNA_26), SEQ ID NO 045 (siRNA_27), SEQ ID NO 046 (siRNA_28), SEQ ID NO 047 (siRNA_29), SEQ ID NO 048 (siRNA_30), SEQ ID NO 049 (siRNA_31), SEQ ID NO 050 (siRNA_32), SEQ ID NO 051 (siRNA_33), SEQ ID NO 052 (siRNA_34), SEQ ID NO 053 (siRNA_35), SEQ ID NO 054 (siRNA_36), SEQ ID NO 055 (siRNA_37), SEQ ID NO 056 (siRNA_38), SEQ ID NO 057 (siRNA_39), SEQ ID NO 058 (siRNA_40), SEQ ID NO 059 (siRNA_41), SEQ ID NO 060 (siRNA_42), SEQ ID NO 061 (siRNA_43), SEQ ID NO 062 (siRNA_44), SEQ ID NO 063 (siRNA_45), SEQ ID NO 064 (siRNA_46), SEQ ID NO 065 (siRNA_47), SEQ ID NO 066 (siRNA_48), SEQ ID NO 067 (siRNA_49), and SEQ ID NO 068 (siRNA_50).

In certain embodiments, the siRNA is provided for use in a method of treatment of hemophilia A.

In certain embodiments, the siRNA is provided for use in a method of treatment of hemophilia B.

Similarly within the scope of the present invention is a method for treating hemophilia in a patient in need thereof, comprising administering to the patient a molecule comprising a siRNA according to the invention.

Similarly, a dosage form for the prevention or treatment of hemophilia is provided, comprising a molecule comprising a siRNA according to the invention.

In the context of the present specification, the expression "a molecule comprising a siRNA according to the invention", is meant to encompass a siRNA according to the invention and a molecule, in particular a dsRNA molecule, from which a siRNA according to the according to the invention can be generated within a mammalian cell by the RNA interference pathway.

"Nucleotides" in the context of the present invention are nucleic acid or nucleic acid analogue building blocks, oligomers of which are capable of forming selective hybrids with RNA oligomers on the basis of base pairing. The term nucleotides in this context includes the classic ribonucleotide building blocks adenosine, guanosine, uridine (and ribosylthymin), cytidine, the classic deoxyribonucleotides deoxyadenosine, deoxyguanosine, thymidine, deoxyuridine and deoxycytidine. It further includes analogues of nucleic acids such as phosphotioates, 2'O-methylphosphothioates, peptide nucleic acids (PNA; N-(2-aminoethyl)-glycine units linked by peptide linkage, with the nucleobase attached to the alpha-carbon of the glycine) or locked nucleic acids (LNA; 2'O, 4'C methylene bridged RNA building blocks). The hybridizing sequence may be composed of any of the above nucleotides, or mixtures thereof.

In certain embodiments, the hybridizing sequence of the siRNA according to the invention comprises 17, 18, 19, 20, 21, 22, 23, 24, 25, 26 or 27 nucleotides.

In certain embodiments, the hybridizing sequence is at least 95% identical, more preferred 96%, 97%, 98%, 99% or 100% identical to the reverse complimentary sequence of SEQ ID 001 or SEQ ID 002. In certain embodiments, the hybridizing sequence comprises deoxynucleotides, phosphothioate deoxynucleotides, LNA and/or PNA nucleotides or mixtures thereof.

In the context of the present specification, the terms sequence identity and percentage of sequence identity refer to the values determined by comparing two aligned sequences. Methods for alignment of sequences for comparison are well-known in the art. Alignment of sequences for comparison may be conducted by the local homology algorithm of Smith and Waterman, Adv. Appl. Math. 2:482 (1981), by the global alignment algorithm of Needleman and Wunsch, J. Mol. Biol. 48:443 (1970), by the search for similarity method of Pearson and Lipman, Proc. Nat. Acad. Sci. 85:2444 (1988) or by computerized implementations of these algorithms, including, but not limited to: CLUSTAL, GAP, BESTFIT, BLAST, FASTA and TFASTA. Software for performing BLAST analyses is publicly available, e.g., through the National Center for Biotechnology-Information (http://blast.ncbi.nlm.nih.gov/).

One example for comparison of amino acid sequences is the BLASTP algorithm that uses the default settings: Expect threshold: 10; Word size: 3; Max matches in a query range: 0; Matrix: BLOSUM62; Gap Costs: Existence 11, Extension 1; Compositional adjustments: Conditional compositional score matrix adjustment. One such example for comparison of nucleic acid sequences is the BLASTN algorithm that uses the default settings: Expect threshold: 10; Word size: 28; Max matches in a query range: 0; Match/Mismatch Scores: 1.-2; Gap costs: Linear. Unless otherwise stated, sequence identity values provided herein refer to the value obtained using the BLAST suite of programs (Altschul et al., J. Mol. Biol. 215:403-410 (1990)) using the above identified default parameters for protein and nucleic acid comparison, respectively.

In some embodiments, the hybridizing sequence comprises ribonucleotides, phosphothioate and/or 2'-O-methyl-modified phosphothioate ribonucleotides.

In some embodiments, the hybridizing sequence comprises deoxynucleotides, phosphothioate deoxynucleotides, phosphothioate ribonucleotides and/or 2'-O-methyl-modified phosphothioate ribonucleotides.

Wherever alternatives for single separable features are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

DESCRIPTION OF THE FIGURES

FIG. 3 shows tail bleeding models. Blood was collected after 2 mm (A) and 4 mm (B) tail transection for 30 min (A) and 10 min (B) in a fresh tube of saline; total blood loss (µl) was then measured. $F8^{+/-}Pros1^{+/+}$ and $F8^{+/+}Pros1^{+/+}$ mice (white columns) served as controls (n=5 for all groups in A, n=6 for all groups in A). C, An anti-human PS antibody altered tail bleeding after 4 mm transection.

FIG. 5 shows that both PS and TFPI are expressed in murine synovium. A, Immunostaining for PS and TFPI in the knee intra-articular space of injured knees from $F8^{-/-}$ $Pros1^{+/+}$ mice previously treated with Ctrl-siRNA or mPS-siRNA. Arrow heads point to synovial tissue and arrows, to vascular structures, all positive for both PS and TFPI. Boxes in the upper figures (Scale bars: 200 µm) show the area enlarged in the panel below (Scale bars: 50 µm). B, Immunostaining for TFPI in the knee intra-articular space of not injured knees from $F8^{-/-}$ $Pros1^{+/+}$ and $F8^{-/-}Pros1^{-/-}$ mice. C-E, Western blot analysis of conditioned media from primary murine fibroblast-like synoviocytes (FLS) cultures using anti-PS (c) and anti-TFPI (d) antibodies. Platelet-free plasma (PFP), protein lysates from platelets (PLT), murine PS (mPS) were used as positive controls (c). TFPI isoform expression determined by comparing molecular weights of deglycosylated TFPI and of fully glycosylated TFPI. Murine placenta was used as positive control for TFPIα. E-F, Western blot analysis of total protein lysates isolated from FLS after 24 h of culture in presence of thrombin (Thr, +) or of a vehicle (−) using anti-PS (f) and anti-TFPI (e) antibodies. Human recombinant TFPI full length was used as positive control for TFPIα (hrTFPI). Blots are representative of three independent experiments.

EXAMPLES

Figure 1:
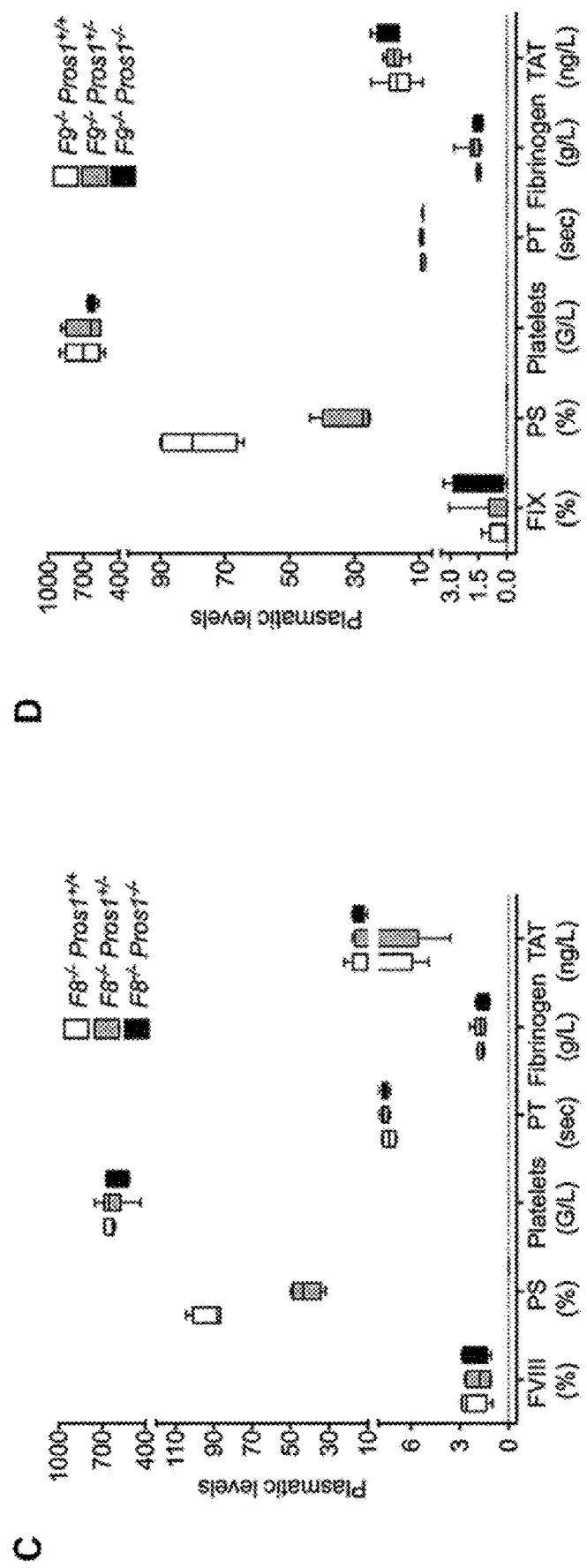
FIG. 1 shows that loss of X-ase activity rescues $Pros1^{-/-}$ mice. A, Schematic model of thrombin generation in hemophilic condition. One of the major coagulation complexes is the intrinsic tenase (X-ase) complex. X-ase comprises activated FIX (FIXa) as the protease, activated FVIII (FVIIIa) as the cofactor, and factor X (FX) as the substrate. Although the generation or exposure of tissue factor (TF) at the site of injury is the primary event in initiating coagulation via the extrinsic pathway, the intrinsic pathway X-ase is important because of the limited amount of available active TF in vivo and the presence of TFPI which, when complexed with activated FX (FXa), inhibits the TF/activated factor VII (FVIIa) complex (FIG. 1a). Thus, sustained thrombin generation depends upon the activation of both FIX and FVIII (FIG. 1a). This process is amplified because FVIII is activated by both FXa and thrombin, and FIX, by both FVIIa and activated factor XI (FXIa), the latter factor being previously activated by thrombin. Consequently, a progressive increase in FVIII and FIX activation occurs as FXa and thrombin are formed B, the experimental approach to enhance thrombin generation in severe hemophilia A and B by targeting Pros1. C-D, Murine model validation and evaluation of DIC hematologic parameters in hemophilic adult mice with and without Pros1 deficiency: PS (antigenic), FVIII (coagulant activity) or FIX (coagulant activity) plasma levels in $F8^{-/-}Pros1^{+/+}$, $F8^{-/-}Pros1^{+/-}$ and $F8^{-/-}Pros1^{-/-}$ (C), and $F9^{-/-}Pros1^{+/+}$, $F9^{-/-}Pros1^{+/-}$ and $F9^{-/-}Pros1^{-/-}$ adult mice (D) (n=5/group); platelets (n=7/group), fibrinogen (n=8/group), PT (n=6/group) and TAT (n=6/group) in hemophilia A group (c); and platelets (n=5/group), fibrinogen (n=4/group), PT (n=4/group) and TAT (n=4/group) in hemophilia B group (D). E-F, Macroscopic image of lungs from $F8^{-/-}Pros1^{-/-}$ mice 24 h after a single intravenous injection of 2 U/g recombinant FVIII (Advate®) infusion (E) and corresponding microscopic evaluation of fibrin clots in lung section (F). G, Recombinant FVIII (Advate®) administration in $F8^{-/-}Pros1^{+/+}$ and $F8^{-/-}Pros1^{-/-}$: plasma levels of fibrinogen and TAT at 24 h following 5 injection of 0.3 U/g Advate® i.v. (injection time-points: 1 h before catheter insertion and 1 h, 4 h, 8 h and 16 h after catheter insertion) (n=3) (G, white and black columns) and 24 h after a single i.v. injection in $F8^{-/-}Pros1^{-/-}$ (n=3) (G, dashed column), and representative immunohistochemistry allowing the detection of fibrin clots in lungs and liver sections in $F8^{-/-}Pros1^{-/-}$ 24 h after 0.3 U/g repeated i.v. injections of Advate® (H) and after a single i.v. injection of 0.3 U/g Advate® i.v. (i). All data are expressed as mean±s.e.m.; ns, not significant; *, P<0.05**; P<0.005.
Figure 1:
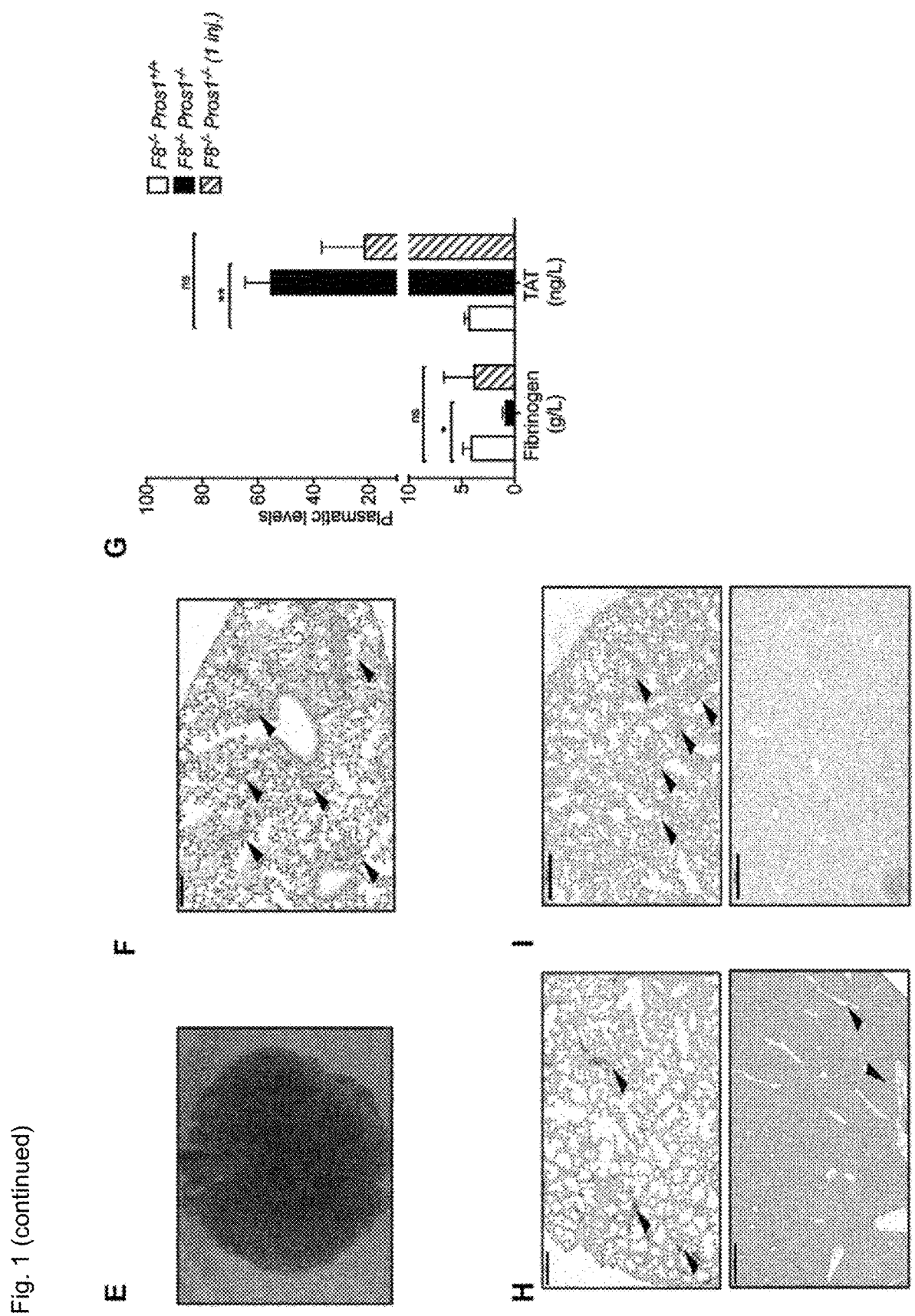
Figure 8:
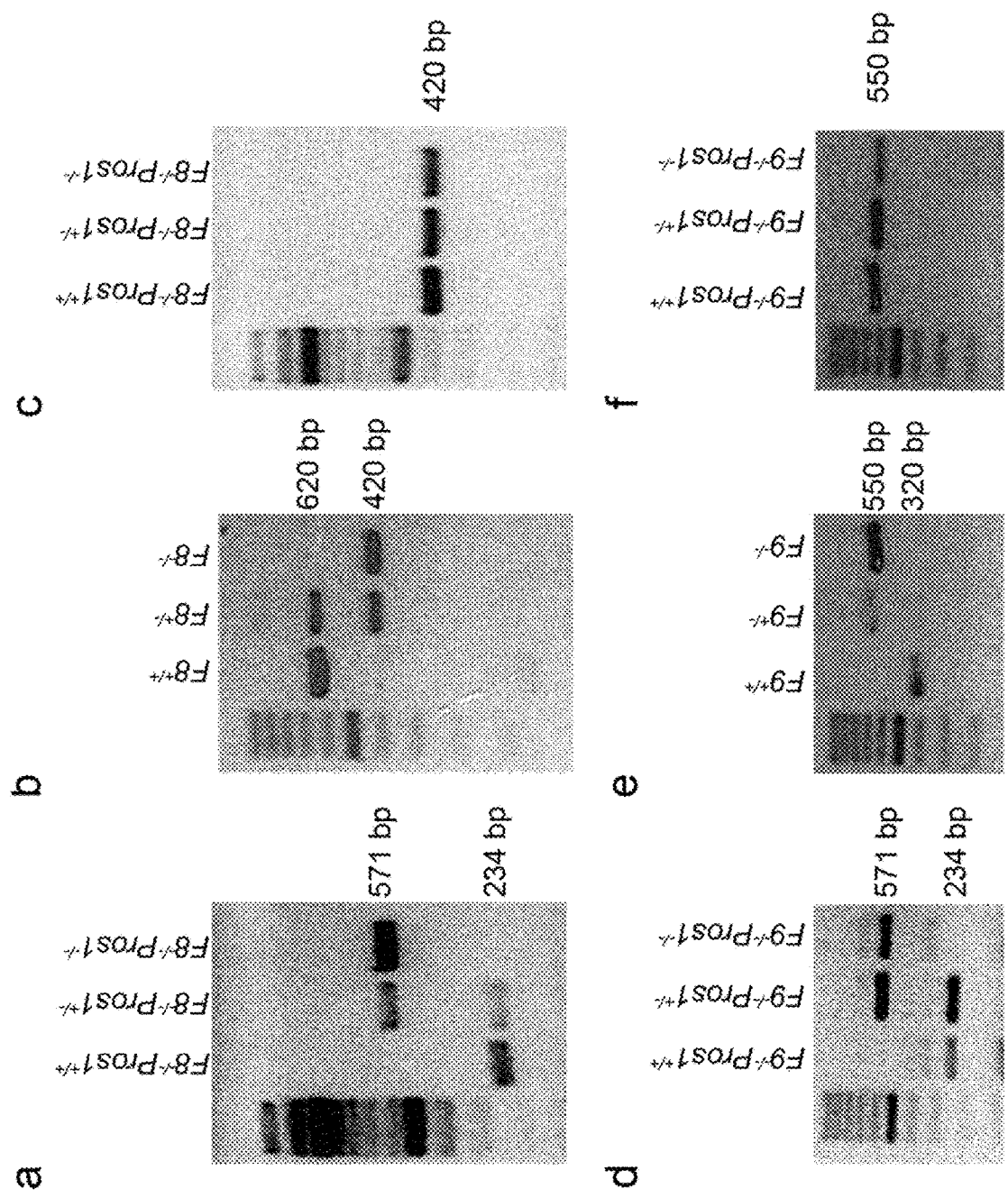
FIG. 8 shows genotyping approaches. Genotypes obtained by crossing $F8^{-/-}Pros1^{+/-}$ (a-c) and $F9^{-/-}Pros1^{+/-}$ (d-f) mice. a, Pros1 alleles were amplified by a multiplex PCR. PCR products were then subjected to electrophoresis; the wt band has a lower molecular weight (234 bp) compared to the null band (571 bp), in accordance to Saller, 2009. b, Set-up of multiplex PCR to amplify the wt band (620 bp) and the null band (420 bp) of F8 alleles from genomic DNA. c, PCR products of F8 alleles amplification (null band: 420 bp) on the same samples than in (a). d, Pros1 alleles were amplified by a multiplex PCR. PCR products were then subjected to electrophoresis; the wt band has a lower molecular weight (234 bp) compared to the null band (571 bp), in accordance to Saller, 2009. e, Set-up of multiplex PCR to amplify the wt band (320 bp) and the null band (550 bp) of F9 alleles from genomic DNA. f, PCR products of F9 alleles amplification (null band: 550 bp) on the same samples than in (d).

Example 1: Loss of X-Ase Activity Rescues $Pros1^{-/-}$ Mice $Pros1^{+/-}$ females crossed with $F8^{-/-}$ males produced 25% $F8^{+/-}Pros1^{+/-}$ progeny. $F8^{+/-}Pros1^{+/-}$ females bred with $F8^{-/-}$ males resulted in 25% $F8^{-/-}Pros1^{+/-}$ progeny (FIG. 8A-C). Similar observations were made with $F9^{-/-}Pros1^{+/-}$ mice (FIG. 8D-F). As expected, $F8^{-/-}Pros1^{-/-}$ and $F9^{-/-}Pros1^{-/-}$ mice did not display FVIII and FIX plasma activity, respectively, and PS was not detected in $F8^{-/-}Pros1^{-/-}$ and $F9^{-/-}Pros1^{-/-}$ mice plasma (FIG. 1C-D). PS levels in $F8^{-/-}Pros1^{+/-}$ and $F9^{-/-}Pros1^{+/-}$ were ~50-60% less than in $F8^{-/-}Pros1^{+/+}$ and $F9^{-/-}Pros1^{+/+}$ mice (FIG. 1C-D), as reported.

Of 295 pups from $F8^{+/-}Pros1^{+/-}$ breeding pairs, 72 (24%) were $F8^{-/-}Pros1^{+/+}$, 164 (56%) were $F8^{-/-}Pros1^{+/-}$ and 59 (20%) were $F8^{-/-}Pros1^{-/-}$ ($\chi^2$=4.8, P=0.09). Thus, $F8^{-/-}Pros1^{-/-}$ mice were present at the expected Mendelian ratio. In contrast, of 219 pups from $F9^{-/-}Pros1^{+/-}$ breeding pairs, 56 (26%) were $F9^{-/-}Pros1^{+/+}$, 132 (60%) were $F9^{-/-}Pros1^{+/-}$ and 31 (14%) were $F9^{-/-}$ $Pros1^{-/-}$ ($\chi^2$=14.95, P=0.001). This is compatible with a transmission ratio distortion for $F9^{-/-}$ $Pros1^{-/-}$ mice consistent with the decreased litter sizes compared to those of matings from $F9^{+/+}Pros1^{+/+}$ mice (5.2±0.7 versus 9.8±1.8, n=4 matings/over $3^r$ generations, P=0.046).

$F8^{-/-}Pros1^{-/-}$ and $F9^{-/-}Pros1^{-/-}$ mice appeared completely normal. Their viability was monitored up to 20 (n=4) and 16 months (n=2), respectively, without showing any difference compared to $F8^{-/-}Pros1^{+/+}$ and $F9^{-/-}Pros1^{+/+}$ mice, respectively.

Figure 9:
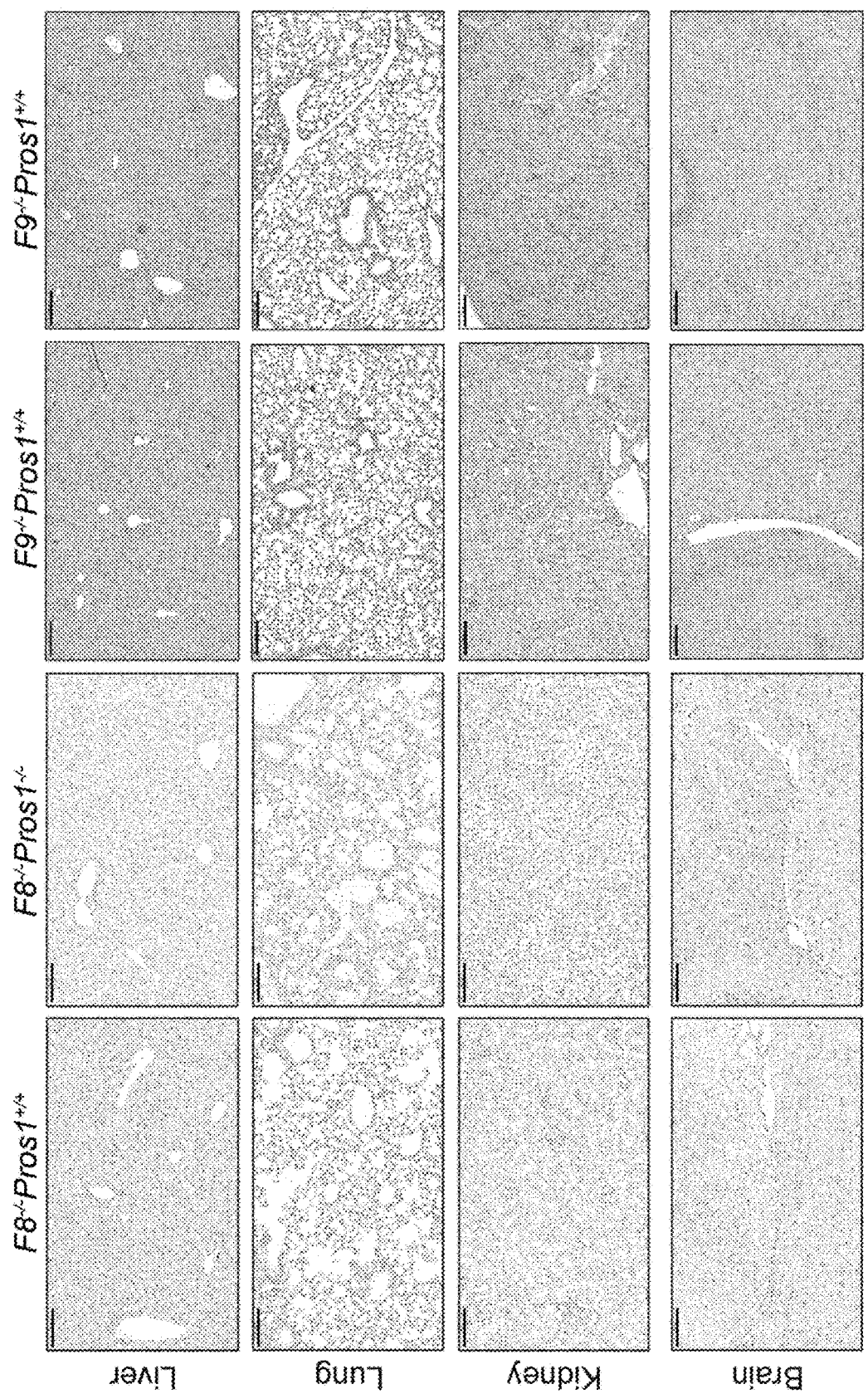
FIG. 9 shows histology in physiologic condition. Immunostaining for insoluble fibrin on liver, lung, kidney, brain sections in $F8^{-/-}Pros1^{-/-}$ and in $F8^{-/-}Pros1^{+/+}$ mice as well as in $F9^{-/-}Pros1^{+/+}$ and $F9^{-/-}Pros1-/-$. Scale bar: 100 µm.
Figure 10:
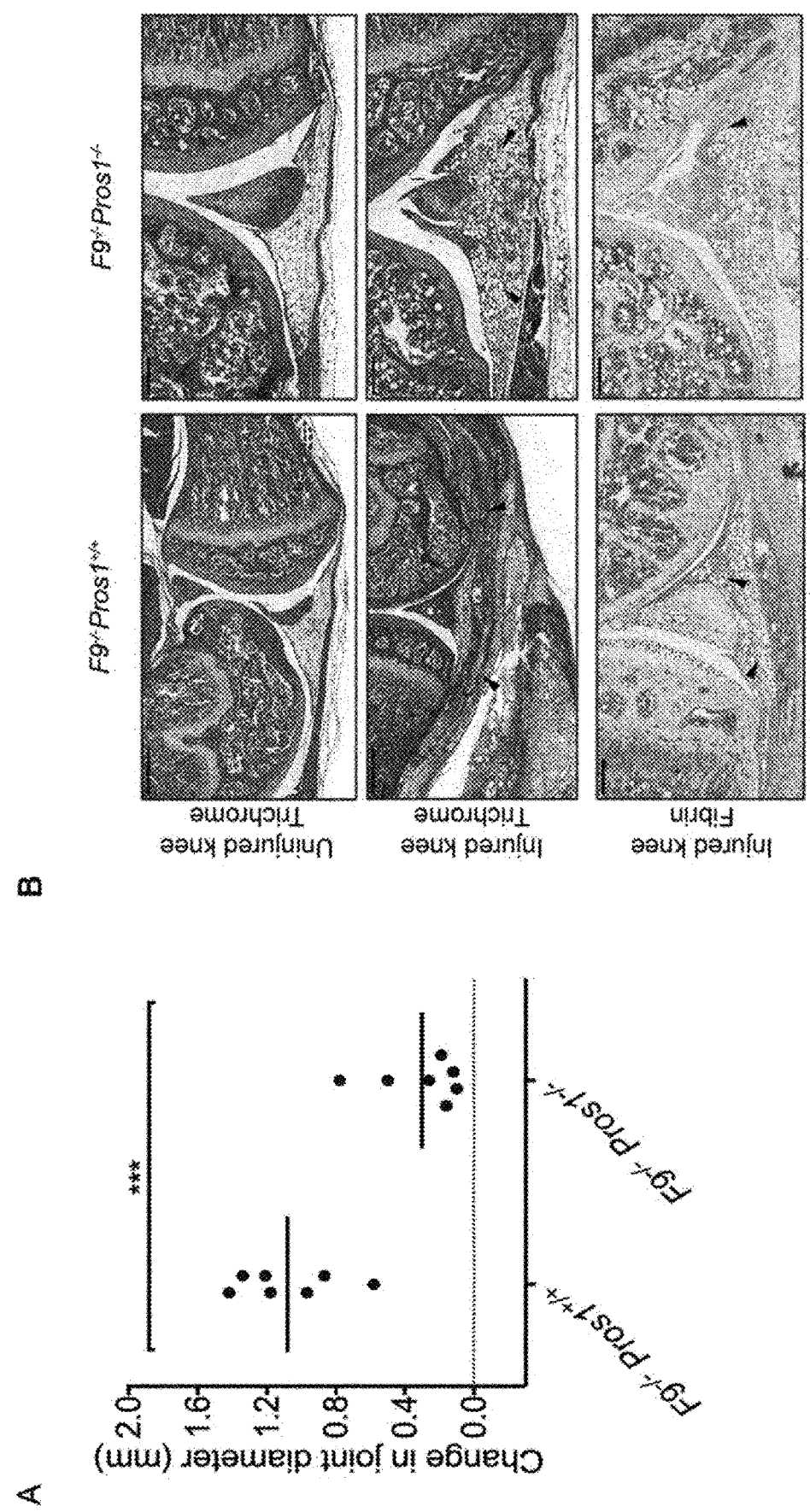
FIG. 10 shows that genetic loss of Pros1 prevents hemarthrosis in mice with hemophilia B. A, Difference between the knee diameter 72 h after the injury and before the injury in $F9^{-/-}$ $Pros1^{+/+}$, $F9^{-/-}Pros1^{+/-}$, $F9^{-/-}Pros1^{-/-}$ and $F9^{+/+}$ $Pros1^{+/+}$ mice. B, Microscopic evaluation (Masson's trichrome stain and staining for insoluble fibrin, mAb clone 102-10) of the knee intra-articular space of a representative not injured and injured legs after 72 h in $F9^{+/+}Pros1^{+/+}$, $F9^{-/-}Pros1^{+/+}$ and $F9^{-/-}Pros1^{-/-}$ mice. Scale bar: 500 µm. Measurements are presented as mean±s.e.m. \*\*\*, P<0.0005.

As a complete Pros1 deficiency in mice leads to consumptive coagulopathy[15], we assessed whether $F8^{-/-}$ $Pros1^{-/-}$ and $F9^{-/-}/Pros1^{-/-}$ mice developed DIC. DIC parameters were comparable in $F8^{-/-}Pros1^{+/+}$, $F8^{-/-}Pros1^{+/-}$ and $F8^{-/-}Pros1^{-/-}$ mice (FIG. 10), and in $F9^{-/-}/Pros1^{+/+}$, $F9^{-/-}/Pros1^{+/-}$ and $F9^{-/-}Pros1^{-/-}$ mice (FIG. 1D). Activated partial thromboplastin time (aPTT) was equally prolonged in $F8^{-/-}Pros1^{+/+}$ (69±2 sec), $F8^{-/-}Pros1^{+/-}$ (68±3 sec) and $F8^{-/-}Pros1^{-/-}$ (63±3 sec) mice (mean±s.e.m., n=6 per group, P=0.3) because of the absence of FVIII. Comparable data were obtained with $F9^{-/-}/Pros1^{+/+}$, $F9^{-/-}Pros1^{+/-}$ and $F9^{-/-}$ $Pros1^{-/-}$ mice. Moreover, no thrombosis or fibrin deposition was found in brain, lungs, liver and kidney of $F8^{-/-}Pros1^{-/-}$ and $F9^{-/-}Pros1^{-/-}$ mice (FIG. 9).

Therefore, loss of X-ase activity rescues the embryonic lethality of complete Pros1 deficiency. However, the rescue was only partial with the loss of FIX activity. A possible explanation is that severe HB appears to be a less serious condition compared to severe HA. Consequently, F9 disruption in $Pros1^{-/-}$ mice was less efficient in rebalancing coagulation than F8 disruption.

To explore whether restoring intrinsic X-ase activity by FVIII infusion induces DIC, thrombosis and purpura fulminans in $F8^{-/-}Pros1^{-/-}$ mice, we administered recombinant FVIII (rFVIII) intravenously. No mouse died following rFVIII injection. Thrombi in numerous blood vessels and bleeding in the lungs were found in $F8^{-/-}Pros1^{-/-}$ mice 24 h after a single injection of an overdose of rFVIII (FIG. 1E-F). Twenty-four h after repeated administration of a normal dose of rFVIII, coagulation analyses showed incoagulable prothrombin time (PT) (not shown), low fibrinogen and high thrombin-antithrombin (TAT) levels, compatible with an overt DIC (FIG. 1G). In contrast, after a single injection of a normal dose of rFVIII in $F8^{-/-}Pros1^{-/-}$ mice, fibrinogen and TAT levels were comparable to those of untreated $F8^{-/-}Pros1^{-/-}$ mice (FIG. 1G). Although numerous thrombi were visible in lungs and liver (FIG. 1H-I), none of these mice developed purpura fulminans.

Figure 2:
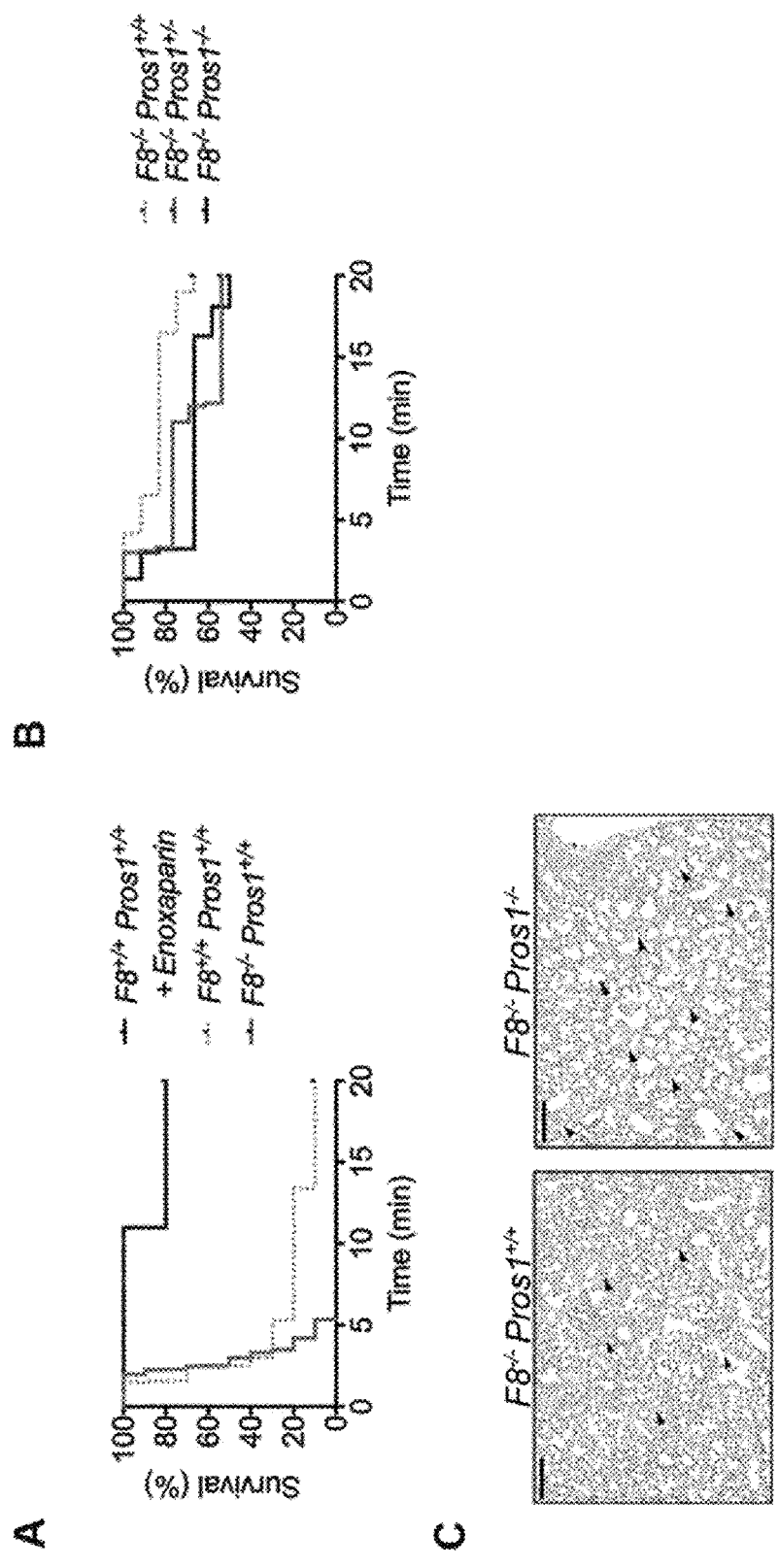
FIG. 2 shows murine models of thrombosis. A-C, TF-induced venous thromboembolism in $F8^{+/+}$ $Pros1^{+/+}$, $F8^{-/-}$ $Pros1^{+/+}$, $F8^{-/-}$ $Pros1^{+/-}$ and $F8^{-/-}$ $Pros1^{-/-}$ mice (n=10/genotype). Anesthetized mice were injected intravenously via the inferior vena cava with different doses of recombinant TF (Innovin): ½ dilution (~4.3 nM TF) in A and ¼ dilution (~2.1 nM TF) in B-C. In (A), one group of $F8^{+/+}$ $Pros1^{+/+}$ mice received an injection of the low molecular weight heparin (enoxaparin 60 µg/g s.c.). The time to the onset of respiratory arrest that lasted at least 2 min was recorded. Experiments were terminated at 20 min. Kaplan-Meier survival curves (A-B). C, 2 min after onset of respiratory arrest or at the completion of the 20-min observation period, lungs were excised and investigated for fibrin clots (immunostaining for insoluble fibrin, mAb clone 102-10). D, Thrombus formation in $FeCl_3$-injured mesenteric arteries recorded by intravital microscopy in $F8^{+/+}$ $Pros1^{+/+}$, $F8^{-/-}$ $Pros1^{+/+}$ and $F8^{-/-}$ $Pros1^{-/-}$ mice, representative experiment (n=3/genotype). D, Thrombus formation in $FeCl_3$-injured mesenteric arteries recorded by intravital microscopy in $F8^{+/+}$ $Pros1^{+/+}$, $F8^{-/-}$ $Pros1^{+/+}$ and $F8^{-/-}$ $Pros1^{-/-}$ mice, representative experiment (n=3/genotype).
Figure 2:
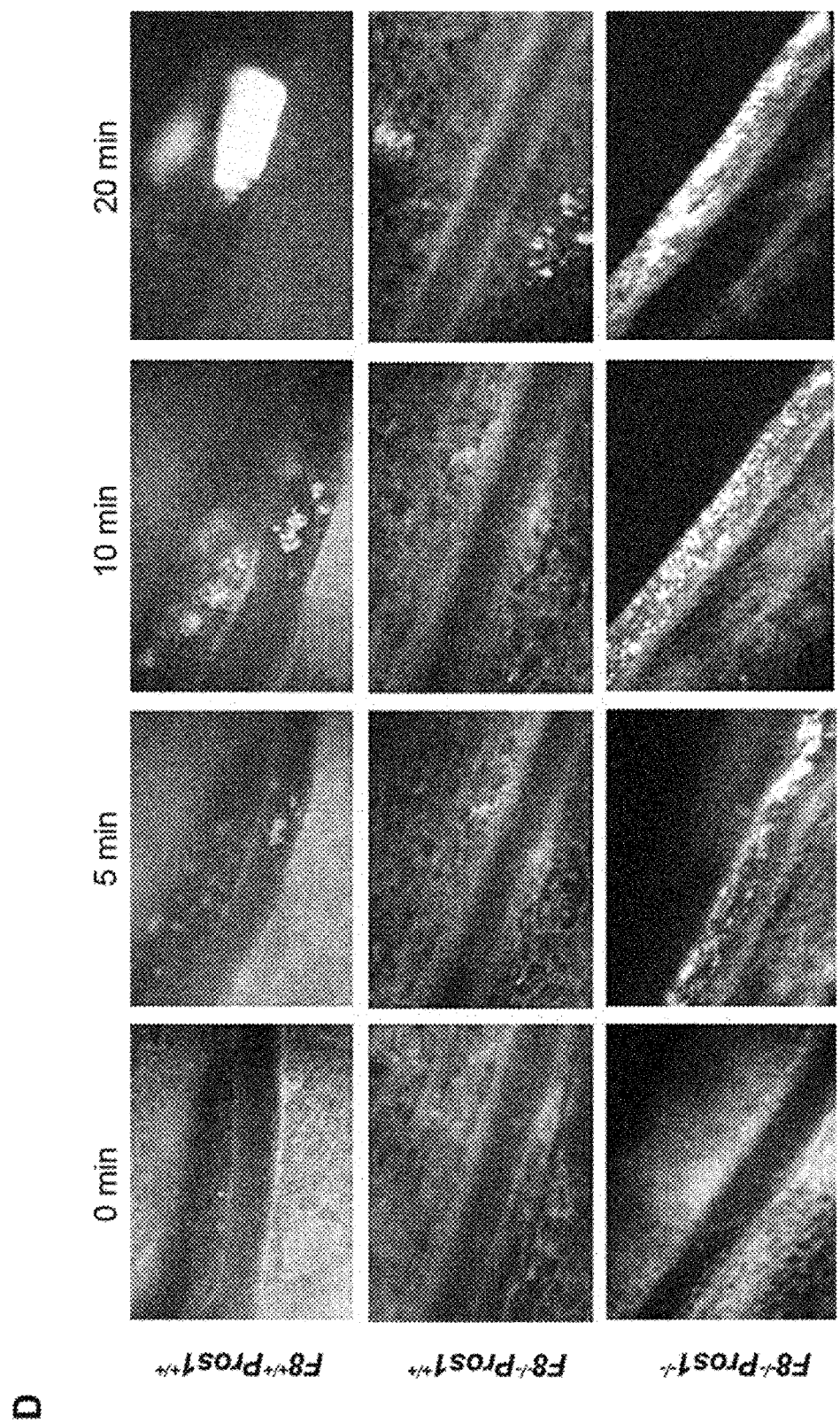

Example 2: Loss of X-Ase Activity does not Prevent Lethality Caused by TF-Induced Thromboembolism in $Pros1^{-/-}$ Mice We demonstrated previously that, although 88% of $Pros1^{+/+}$ mice survived to a TF-induced thromboembolism model, only 25% of $Pros1^{+/-}$ mice were still alive 20 min after a low TF dose injection (~1.1 nM). When using a higher TF dosage (~4.3 nM), both $Pros1^{+/+}$ and $Pros1^{+/-}$ mice died within 20 min. However, $Pros1^{+/-}$ died earlier than $Pros1^{+/+}$. HA and WT mice were equally sensitive to this high TF-dose with more than 85% of them succumbing within 15 min (FIG. 2A). In contrast, >75% WT mice under thromboprophylaxis with a low molecular weight heparin (LMWH) survived (FIG. 2A). Thus, in contrast with LMWH, HA does not protect mice against TF-induced thromboembolism. We then investigated $F8^{-/-}Pros1^{+/+}$, $F8^{-/-}Pros1^{+/-}$ and $F8^{-/-}Pros1^{-/-}$ mice in the same model. After the infusion of TF (~2.1 nM), 40-60% of the mice died (P>0.05), independently of their Pros1 genotype (FIG. 2B). However, there was a trend for $F8^{-/-}Pros1^{-/-}$ and $F8^{-/-}Pros1^{+/-}$ succumbing earlier than $F8^{-/-}Pros1^{+/+}$ mice, and for $F8^{-/-}Pros1^{+/-}$ dying earlier than $F8^{-/-}Pros1^{+/+}$ mice (mean time to death: 12±4 min for $F8^{-/-}Pros1^{+/+}$, 7±2 min for $F8^{-/-}Pros1^{+/-}$, 8±3 min for $F8^{-/-}Pros1^{-/-}$ mice, n=4-6/group, P=0.43). Similar data were obtained with $F9^{-/-}Pros1^{+/+}$, $F9^{-/-}Pros1^{+/-}$ and $F9^{-/-}Pros1^{-/-}$ mice (data not shown).

Fibrin clots were detected in lung arteries of $F8^{-/-}Pros1^{+/+}$ and $F8^{-/-}Pros1^{-/-}$ mice that died during the TF-induced thromboembolic challenge (FIG. 2C). Importantly, there were more thrombi in lungs from $F8^{-/-}Pros1^{-/-}$ than from $F8^{-/-}Pros1^{+/+}$ mice (n=48 versus 26, respectively). Moreover, most arteries in $F8^{-/-}Pros1^{-/-}$ lungs were completely occluded while they were only partially occluded in $F8^{-/-}Pros1^{+/+}$ lungs.

None of the $F8^{-/-}Pros1^{-/-}$ mice that succumbed during the TF-induced thromboembolic-challenge developed purpura fulminans. Similar data were obtained with $F9^{-/-}Pros1^{+/+}$, $F9^{-/-}Pros1^{+/-}$ and $F9^{-/-}Pros1^{-/-}$ mice (not shown).

Example 3: Loss of FVIII Partially Protects $Pros1^{-/-}$ Mice Against Thrombosis in Mesenteric Arterioles We then recorded thrombus formation in mesenteric arterioles, a model sensitive to defects in the intrinsic pathway of coagulation. In $F9^{+/+}Pros1^{+/+}$ mice, thrombi grew to occlusive size in 20 min, and all injured arterioles were occluded (FIG. 2D). As expected, none of the arterioles of $F8^{-/-}Pros1^{+/+}$ displayed thrombosis, whereas $F8^{-/-}Pros1^{-/-}$ mice showed partial thrombi (FIG. 2D).

Emboli were generated during thrombus formation in $F9^{+/+}Pros1^{+/+}$ mice, but not in $F8^{-/-}Pros1^{+/+}$ mice. In $F8^{-/-}Pros1^{-/-}$ mice, multiple micro-emboli detached during partial thrombus growth, preventing the formation of occlusive thrombi.

Example 4: Pros1 Targeting Limits but does not Abrogate Tail Bleeding in Mice with HA The bleeding phenotype was assessed by tail transection using a mild or a severe bleeding model.

In both models, blood loss was reduced in $F8^{-/-}Pros1^{-/-}$ compared to $F8^{-/-}Pros1^{+/+}$ mice (FIG. 3A-B). When challenged by the mild model, $F8^{-/-}Pros1^{+/-}$ mice bled less than $F8^{-/-}Pros1^{+/+}$ mice (FIG. 3A). In contrast, when exposed to the severe model, $F8^{-/-}Pros1^{-/-}$ and $F8^{-/-}Pros1^{+/-}$ mice displayed comparable blood loss (FIG. 3B). However, $F8^{-/-}Pros1^{-/-}$ mice bled more than $F8^{+/-}Pros1^{+/+}$ and $F9^{+/+}Pros1^{+/+}$ mice in both models (FIG. 3A-B), indicating that the loss of Pros1 in $F8^{-/-}$ mice did only partially correct the bleeding phenotype of $F8^{-/-}$ mice.

Then, an PS-neutralizing antibody was used to investigate how inhibition of PS activity alters tail bleeding in $F8^{-/-}Pros1^{+/-}$ mice. This antibody limited blood loss in $F8^{-/-}Pros1^{+/-}$ mice (FIG. 3C) to the same degree as complete genetic loss of Pros1 (FIG. 3B).

Example 5: Pros1 Targeting or PS Inhibition Fully Protects HA or HB Mice from Acute Hemarthrosis (AH)

Figure 4:
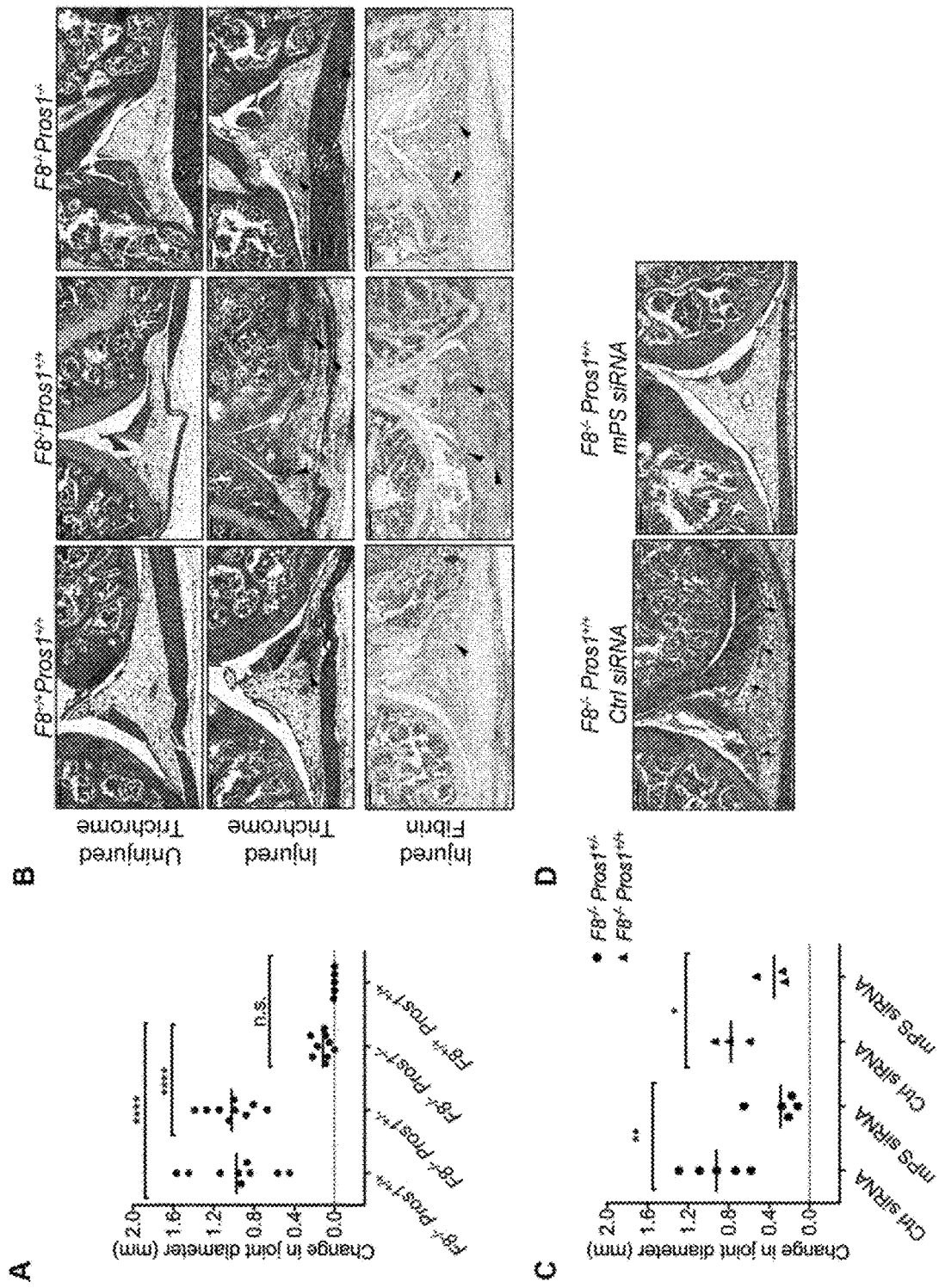
FIG. 4 shows an acute hemarthrosis model. A, Difference between the knee diameter 72 h after the injury and before the injury in $F8^{-/-}Pros1^{+/+}$, $F8^{-/-}Pros1^{+/-}$, $F8^{-/-}Pros1^{-/-}$ and $F8^{+/+}Pros1^{+/+}$ mice. B, Microscopic evaluation (Masson's trichrome stain and immunostaining for insoluble fibrin) of the knee intra-articular space of a representative not injured and injured legs after 72 h in $F8^{+/+}Pros1^{+/+}$, $F8^{-/-}Pros1^{+/+}$ and $F8^{-/-}Pros1^{-/-}$ mice. C, In vivo mPS silencing using specific siRNA: evaluation of the joint diameter 72 h after injury in $F8^{-/-}Pros1^{+/-}$ and $F8^{-/-}$ $Pros1^{+/+}$ mice treated with a single i.p. infusion of mPS siRNA or control siRNA. D, Microscopic evaluation (Masson's trichrome stain) of the knee intra-articular space of a representative injured leg after 72 h in $F8^{-/-}Pros1^{+/+}$ mice previously treated with mPS siRNA or Ctrl siRNA. Measurements are presented as mean±s.e.m. *, P<0.05; , P<0.005; *, P<0.0005; ****, P<0.0001.

Although bleeding may appear anywhere in hemophilia patients, most of hemorrhages occur in the joints. To determine whether Pros1 loss prevents hemarthrosis in hemophilic mice, we applied an AH model to $F8^{-/-}Pros1^{+/+}$, $F8^{-/-}Pros1^{+/-}$, $F8^{-/-}Pros1^{-/-}$ and $F8^{+/+}Pros1^{+/+}$ mice. Knee swelling after injury was reduced in $F8^{-/-}Pros1^{-/-}$ and $F9^{+/+}Pros1^{+/+}$ mice compared to Fe $Pros1^{+/+}$ and $F8^{-/-}Pros1^{+/-}$ mice (FIG. 4A). There was also no difference in knee swelling between $F8^{-/-}Pros1^{-/-}$ and $F9^{+/+}Pros1^{+/+}$ mice (FIG. 4A). Bleeding was observed in the joint space and synovium of $F8^{-/-}Pros1^{+/+}$ (IBS=2, n=5) but not of $F8^{-/-}Pros1^{-/-}$ (IBS=0, n=5) and $F9^{+/+}Pros1^{+/+}$ mice (IBS=0, n=5) (FIG. 4B). There was more fibrin in joint space and synovium from $F8^{-/-}Pros1^{+/+}$ than from $F8^{-/-}Pros1^{-/-}$ and $F9^{+/+}Pros1^{+/+}$ mice (FIG. 4B). Similar data were obtained with $F8^{-/-}Pros1^{+/+}$ and $F9^{-/-}Pros1^{-/-}$ mice (IBS=0, n=3 and IBS=2, n=3, respectively) (FIG. 9A-B).

These results were confirmed by the continuous subcutaneous infusion during 4 days of a PS-neutralizing antibody or a control antibody in $F8^{-/-}Pros1^{+/-}$ mice (starting 1 day before AH induction) (knee swelling in PS-neutralizing antibody group was 0.43±0.07 versus 0.69±0.09 mm in control group, n=9, P=0.04). PS plasma level in PS-neutralizing antibody group was 26±6% versus 45±3% in the controls (n=5, P=0.017). In addition, PS inhibition was alternatively achieved by intravenous injection of a murine PS (mPS) siRNA prior to the AH challenge in $F8^{-/-}Pros1^{+/-}$ and $F8^{-/-}Pros1^{+/+}$ mice (FIG. 4C-D). The IBS assessment confirmed the lack of intra-articular bleeding in $F8^{-/-}Pros1^{+/+}$ mice treated with mPS siRNA (IBS=0.5, n=3) when compared to those treated with control siRNA (IBS=2, n=3), (FIG. 4C). Importantly, PS expression was reduced by mPS siRNA both in plasma (26±3% versus 84±11% in controls, n=3, P=0.006) and in the synovium (FIG. 5A).

Example 6: Both PS and TFPI are Expressed in the Synovium of Mice

To understand the prominent intra-articular hemostatic effect of the genetic loss of Pros1 and PS inhibition in hemophilic mice, knee sections were immunostained for PS and TFPI. PS was mainly present at the lining layer of the synovial tissue of $F8^{-/-}Pros1^{+/+}$ mice with AH treated with control siRNA, whereas synovial staining for PS was remarkably reduced in $F8^{-/-}$ $Pros1^{+/+}$ mice with AH that received mPS siRNA (FIG. 5A). In contrast, TFPI staining was more prominent in synovial tissue from hemophilic mice that received the mPS siRNA than in those that were treated by the control siRNA (FIG. 5a). However, TFPI expression was comparable in synovial lining layer of both $F8^{-/-}Pros1^{+/+}$ and $F8^{-/-}Pros1^{-/-}$ mice (FIG. 5B).

To demonstrate further that PS is expressed by fibroblast-like synoviocytes (FLS), we performed western blots on conditioned media collected from $F9^{+/+}Pros1^{+/+}$, $F8^{-/-}Pros1^{+/+}$ and $F8^{-/-}Pros1^{-/-}$ FLS. As shown in FIG. 5C, media of $F9^{+/+}Pros1^{+/+}$ and $F8^{-/-}Pros1^{+/+}$ FLS displayed a band at a molecular weight ~75 kDa comparable to PS and similar to the one observed in plasma and platelets. As expected, no staining was detected in media obtained from $F9^{+/+}Pros1^{-/-}$ FLS (FIG. 5C).

We also studied TFPI expression in $F8^{-/-}Pros1^{+/+}$ and $F8^{-/-}Pros1^{-/-}$ FLS conditioned media (FIG. 5D). All media displayed a band at ~50 kDa similar to the one observed with placenta lysates. TFPI isoform expression was investigated following protein deglycosylation because fully glycosylated TFPIα and TFPIβ migrate at the same molecular weight[30]. Deglycosylated TFPI from FLS media migrated as a single band at the molecular weight of TFPIα similar to placenta TFPI (positive control for TFPIα) (FIG. 5D). This indicates that FLS express TFPIα but not TFPIβ. Moreover, PS and TFPI expression increased in $F8^{-/-}Pros1^{+/+}$ FLS after stimulation with thrombin (FIG. 5E-F).

Example 7: Both PS and TFPI are Expressed in the Synovium of Patients with HA or HB Human HA, HB and osteoarthritis knee synovial tissues were then analyzed for both PS and TFPI (FIG. 6A). A strong signal was found for TFPI and PS in the synovial lining and sublining layers of HA patients on demand (n=7). By contrast, immunostaining for both PS and TFPI was decreased in HA patients under prophylaxis (n=5). HB patients on demand displayed less signal for both PS and TFPI in the synovial lining and sublining layers (n=4) than HA patients on demand. Sections from osteoarthritis patients (n=7) did not show an intense staining for TFPI and PS similarly to hemophilic patients under prophylaxis. To evaluate which isoform of TFPI is expressed by human FLS, western blotting on conditioned media of human FLS isolated from healthy subjects and patients with osteoarthritis was performed. Similarly to murine FLS, human FLS express TFPIα but not TFPIβ (FIG. 6B).

Example 8: Loss of Pros1 is Responsible for the Lack of TFPI-Dependent PS Activity and Resistance to APC in HA Mice The full protection against AH in HA or HB mice lacking Pros1 or in which PS was inhibited could be explained at least partly by the lack of PS cofactor activity for APC and TFPI in the joint. However, the reason for a partial hemostatic effect of the lack of Pros1 or PS inhibition in HA mice challenged in the tail bleeding models needs to be further investigated.

Ex vivo TF-initiated thrombin generation testing has shown a correlation between the capacity of plasma to generate thrombin and the clinical severity of hemophilia. Therefore, we investigated the impact of Pros1 loss on thrombin generation in plasma of HA mice. TFPI-dependent PS activity was not assessed in platelet-free plasma (PFP) but in platelet-rich plasma (PRP) because TFPI-cofactor activity of PS cannot be demonstrated in mouse plasma using thrombin generation tests. This is explained by the lack of TFPIα in mouse plasma and its presence in mouse platelets.

Figure 7:
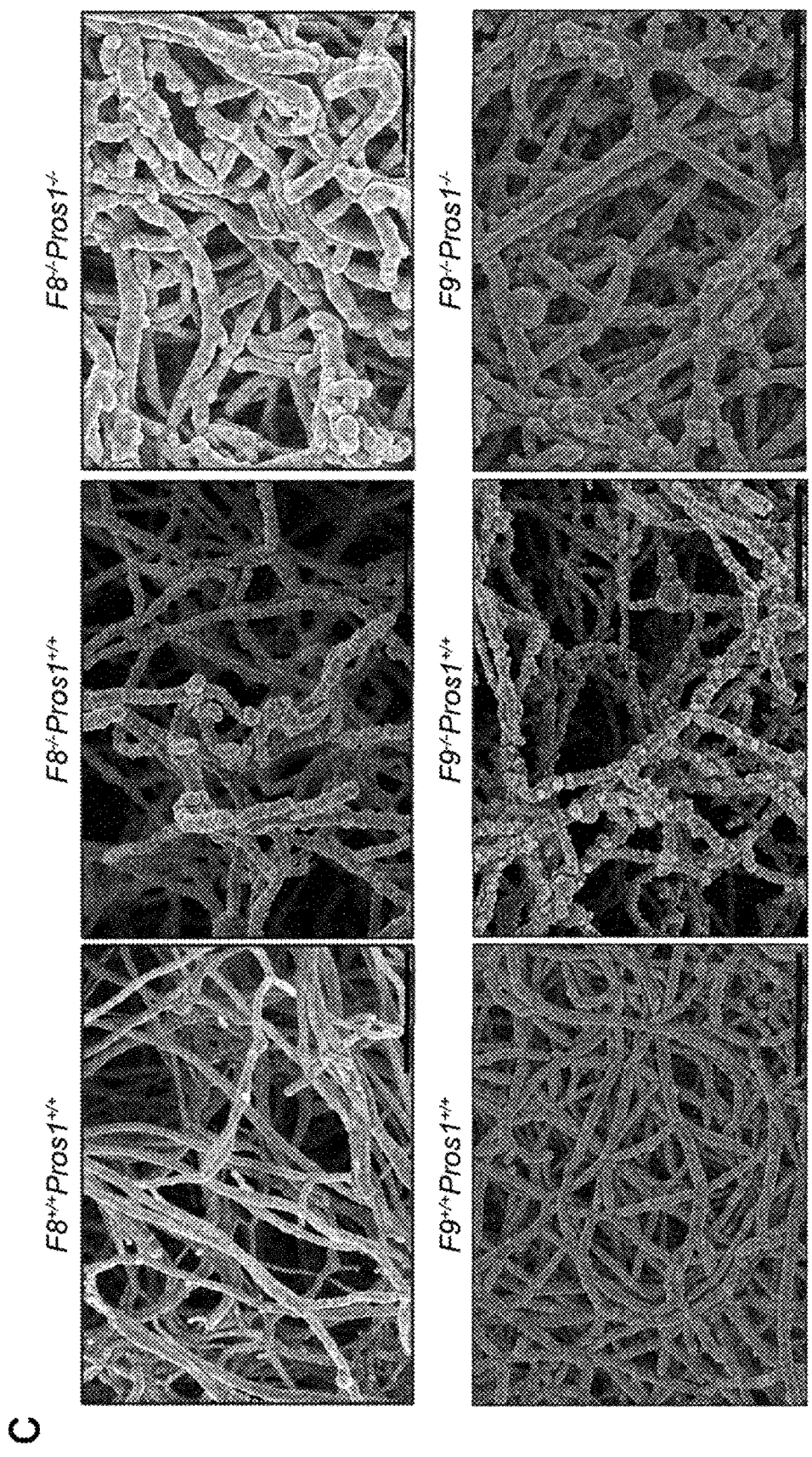
FIG. 7 shows thrombin generation and fibrin network in hemophilia A, TF-(1 pM) induced thrombin generation in PRP from $F8^{-/-}$ $Pros1^{+/+}$ and $F8^{-/-}$ $Pros1^{-/-}$ mice depicting TFPI-dependent PS activity. B, APC-dependent PS activity in PRP and PFP from $F8^{-/-}$ $Pros1^{+/+}$ and $F8^{-/-}$ $Pros1^{-/-}$ mice. C, Representative scanning electron microscopy images from $F8^{+/+}$ $Pros1^{+/+}$, $F8^{-/-}$ $Pros1^{+/+}$ and $F8^{-/-}$ $Pros1^{-/-}$, and from $F9^{+/+}$ $Pros1^{+/+}$, $F9^{-/-}$ $Pros1^{+/+}$ and $F9^{-/-}$ $Pros1^{-/-}$ fibrin structure. D-G, Thrombin generation triggered by low TF concentration (1 pM) in PFP (D-E) and PRP (F-G) from severe HA patients (FVIII<1%) without (D, F) and with a high titer of inhibitor (E, G). Measurements are presented as mean±s.e.m. \*\*, P<0.005, P<0.0005.
Figure 7:
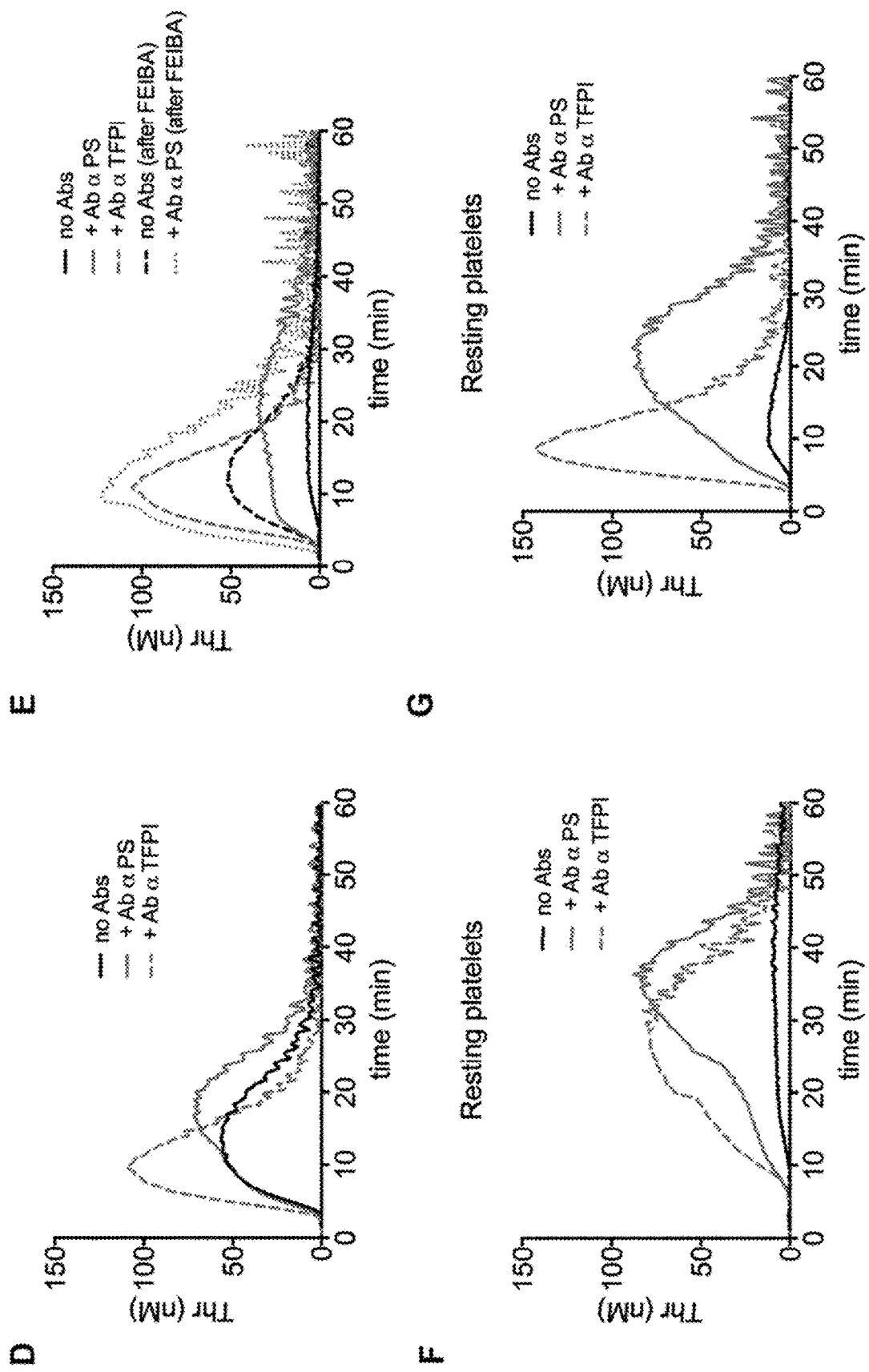

Both thrombin peak and endogenous thrombin potential (ETP) were significantly higher in $F8^{-/-}Pros1^{-/-}$ than in $F8^{-/-}Pros1^{+/+}$ PRP in response to 1 pM TF (1072±160 vs 590±10 nmol/L·min, n=3/group, P=0.04), suggesting the lack of PS TFPI-cofactor activity in $F8^{-/-}Pros1^{-/-}$ PRP (FIG. 7A). Consistent with previous work, both thrombin peak and ETP were comparable in PFP of $F8^{-/-}Pros1^{+/+}$ and $F8^{-/-}Pros1^{-/-}$ mice in presence of 1, 2.5 or 5 pM TF (data not shown).

To assess whether $F8^{-/-}Pros1^{-/-}$ mice exhibited defective functional APC-dependent PS activity, we used thrombin generation testing in $Ca^{2+}$ ionophore-activated PRP in the absence of APC, in the presence of wild-type (WT) recombinant APC, or in the presence of a mutated (L38D) recombinant mouse APC (L38D APC, a variant with ablated PS cofactor activity). In this assay, APC titration showed that the addition of 8 nM WT APC was able to reduce ETP by 90% in activated PRP of WT mice whereas the same concentration of L38D APC diminished ETP by only 30% (data not shown). Based on these data, thrombin generation curves were recorded for activated PRP (3 mice/assay). The calculated APC ratio ($ETP_{+APC\ WT}/ETP_{+APC\ L38D}$) indicated an APC resistance in $F8^{-/-}Pros1^{-/-}$ plasma but not in $F8^{-/-}Pros1^{+/+}$ plasma (0.87±0.13 versus 0.23±0.08, respectively, P=0.01) (FIG. 7B). APC-dependent PS activity was also tested in PFP from $F8^{-/-}Pros1^{+/+}$ and $F8^{-/-}Pros1^{-/-}$ mice (2 mice/assay) in the presence of 2 nM WT APC and L38D APC. Calculated APC ratio showed an APC resistance in $F8^{-/-}Pros1^{-/-}$ but not in $F8^{-/-}Pros1^{+/+}$ mice (1.08±0.04 versus 0.25±0.09, respectively, P=0.0003) (FIG. 7B).

Example 9: Improved Fibrin Network in HA Mice Lacking Pros1 Mice

Figure 11:
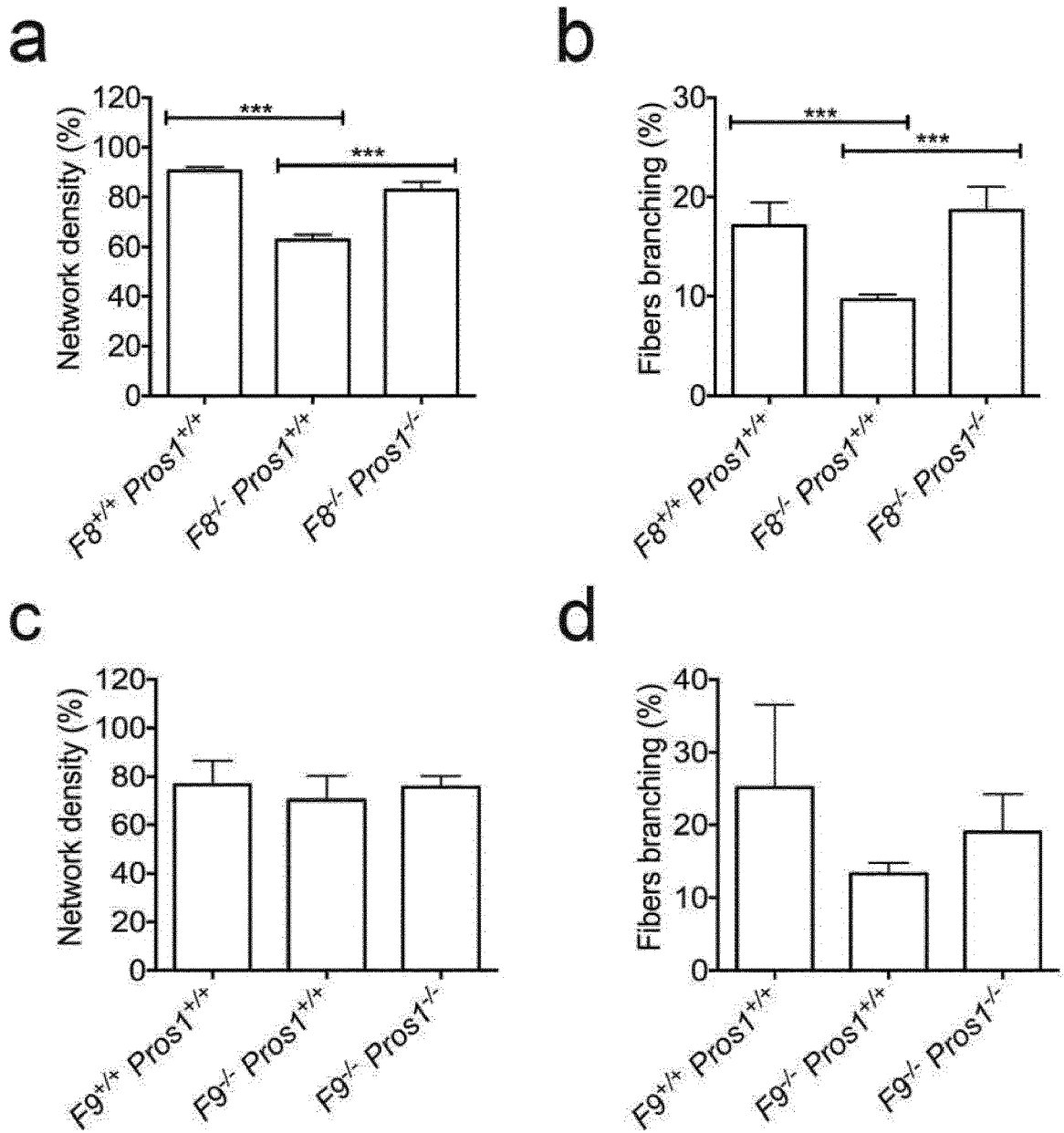
FIG. 11 shows that quantification of fibrin network density and fibers branching. a-b, Fibrin network from $F8^{+/+}$ $Pros1^{+/+}$, $F8^{-/-}$ $Pros1^{+/+}$ and $F8^{-/-}$ $Pros1^{-/-}$ mice. c-d, Fibrin network from $F9^{+/+}$ $Pros1^{+/+}$, $F9^{-/-}$ $Pros1^{+/+}$ and $F8^{-/-}$ $Pros1^{-/-}$. Quantification of fibrin network density (a and c). Quantification of fibers branching (b and d). Measurements are presented as mean±s.e.m. \*\*\*, P<0.0005.

Tail bleeding mouse models are not only sensitive to platelet dysfunction but also to coagulation and fibrinolysis alterations. To understand the differences between studied genotypes regarding tail bleeding, we used scanning electron microscopic imaging to investigate fibrin structure (FIG. 7C). Clots from $F9^{+/+}Pros1^{+/+}$ and $F8^{-/-}Pros1^{-/-}$ plasma showed a denser network of highly branched fibrin fibers compared to $F8^{-/-}Pros1^{+/+}$ plasma clots (FIG. 11a-b). In contrast, clots from $F9^{+/+}Pros1^{+/+}$ and $F9^{-/-}Pros1^{-/-}$ plasma did not display a denser network than $F9^{-/-}Pros1^{+/+}$ plasma clots, but a trend for augmented fibers branching (FIG. 11c-d).

Fibrin fibers from $F8^{-/-}Pros1^{-/-}$ and $F8^{-/-}Pros1^{+/+}$ mice, and from $F9^{-/-}Pros1^{-/-}$ and $F9^{-/-}Pros1^{+/+}$ mice, displayed a larger diameter compared to fibers from $F9^{+/+}Pros1^{+/+}$ mice or $F9^{+/+}Pros1^{+/+}$ mice, respectively. Nevertheless, the fiber surface of $F8^{-/-}Pros1^{-/-}$ and $F9^{-/-}Pros1^{-/-}$ mice showed less porosity as compared to $F8^{-/-}Pros1^{+/+}$ or $F9^{-/-}Pros1^{+/+}$ mice, respectively, suggesting that $F8^{-/-}Pros1^{-/-}$ and $F9^{-/-}$ Pros1$^{+/+}$-derived fibers might be less permeable and thereby more resistant to fibrinolysis than F8$^{-/-}$Pros1$^{+/+}$ or F9$^{-/-}$Pros1$^{+/+}$-derived fibers[38]. These data, in complement to both TFPI and APC cofactor activity results (FIG. 7A-B), help to explain why tail bleeding in F8$^{-/-}$Pros1$^{-/-}$ was improved when compared to F8$^{-/-}$Pros1$^{+/+}$ mice but not completely corrected as in F8$^{+/-}$Pros1$^{+/+}$ mice.

Example 10: PS Inhibition in Plasma Restores Thrombin Generation in Patients with HA We then examined the effect of PS inhibition on thrombin generation in human HA plasma. ETP in PFP increased 2-4-fold in presence of a PS-neutralizing antibody. Similar results were obtained using an anti-human TFPI antibody against the C-terminal domain for efficient FXa inhibition, even in the presence of FVIII inhibitor (FIG. 7D-E). PS inhibition had a remarkable effect in PRP samples where it increased ETP more than 10 times (1912±37 and 1872±64 nM*min) (FIGS. 7F and G, respectively). Thus, PS inhibition completely restored ETP in hemophilic plasma (for comparison, ETP in normal plasma: 1495±2 nM*min). Similar results were obtained using the anti-TFPI antibody (FIG. 7D-G). These data confirm in humans the improvement of thrombin generation in HA PFP and PRP driven by PS inhibition that we observed in mice.

Example 11: Materials and Methods

Mice

F8$^{-/-}$ mice (B6; 129S4-F8$^{tm1Kaz}$/J) and F9$^{-/-}$ mice (B6.129P2-F9$^{tm1Dws}$/J) with C57BL/6J background were obtained from The Jackson Laboratory. Pros1$^{+/-}$ mice were progeny of the original colony[15]. The Swiss Federal Veterinary Office approved the experiments. Mice were genotyped as described[15-17].

TF-Induced Pulmonary Embolism

A model of venous thromboembolism was adapted from Weiss et al[18] with minor modifications[15]. Anesthetized mice, aged 6-9 weeks, received human recombinant TF (hrTF, Dade Innovin, Siemens) intravenously (2 μL/g) at 4.25 nM (1:2 dilution) or 2.1 nM (1:4 dilution). Two minutes after the onset of respiratory arrest or at the completion of the 20-min observation period, lungs were harvested and fixed in 4% PFA. Lung sections were stained with hematoxylin and eosin, and for fibrin. The extent of fibrin clots in the lungs was assessed as number of intravascular thrombi in 10 randomly chosen non overlapping fields (×10 magnification).

Tail Clipping Model in HA Mice

Two different tail clipping models to evaluate bleeding phenotype were assessed as described[14]. Briefly, the distal tail of 8-10 week old mice was transected at 2 mm (mild injury) and the bleeding was venous or at 4 mm (severe injury) and the bleeding was arterial and venous[19]. Bleeding was quantified as blood lost after 30 or 10 min, respectively. In the severe injury model some F8$^{-/-}$Pros1$^{+/-}$ mice received a rabbit anti-human PS-IgG (Dako) or rabbit isotype IgG (R&D Systems) intravenously at a dose of 2.1 mg/kg 2 min before tail transection.

Acute Hemarthrosis Model

Induction of joint bleeding in anesthetized 9-12 week old mice, knee diameter measurements and analgesic coverage were performed according to Øvlisen et al[20]. Joint diameters were measured at 0 and 72 h with a digital caliper (Mitutoyo 547-301, Kanagawa). At 72 h, mice were sacrificed, knees were isolated, fixed in 4% PFA, decalcified and embedded in paraffin. The intra-articular bleeding score (IBS) was assessed as described[21].

In Vivo PS Inhibition 10 week old mice received a continuous infusion of rabbit anti-human PS-IgG (Dako Basel, Switzerland) or rabbit isotype IgG (R&D Systems) at 1 mg/kg/day through subcutaneous osmotic minipumps (model2001, Alzet). Alternatively, 10 week old mice were treated with a single dose of mouse specific siRNA (s72206, Life Technologies) or control siRNA (4459405, In vivo Negative Control #1 Ambion, Life Technologies) at 1 mg/kg using a transfection agent (Invivofectamine 3.0, Invitrogen, Life Technologies) following the manufacturer's instructions. Acute hemarthrosis model was applied 2.5 days after PS inhibition.

Statistical Methods

Values were expressed as mean±sem. Chi-square for non-linked genetic loci was used to assess the Mendelian allele segregation. Survival data in the TF-induced venous thromboembolism model were plotted using the of Kaplan-Meier method. A log-rank test was used to statistically compare the curves (Prism 6.0d; GraphPad). The other data were analyzed by t-test, one-way and two-way ANOVA test with GraphPad Prism 6.0d. A P-value of less than 0.05 was considered statistically significant.

Preparation of Murine Plasma

Mice aged 6-9 weeks were anesthetized with pentobarbital (40 mg/kg), and whole blood was drawn from the inferior vena cava into 3.13% citrate (1 vol anticoagulant/9 vol blood). Blood was centrifuged at 1031 g for 10 min with the centrifuge pre-warmed to 26° C. to obtain platelet rich plasma (PRP). Alternatively blood was centrifuged at 2400 g for 10 min at room temperature (RT), to obtain platelet-poor plasma (PPP). To obtain platelet-free plasma (PFP), an additional centrifugation at 10000 g for 10 min was performed.

Platelet Count and Measurement of Coagulation Parameters

Platelet counts were carried out with an automated cell counter (Procyte Dx Hematology Analyzer, IDEXX). Fibrinogen, FVIII and FIX activity were measured on an automated Sysmex CA-7000 coagulation analyzer (Sysmex Digitana). Prothrombin time (PT) and activated partial thromboplastin time (APTT) were measured on a coagulometer (MC4plus, Merlin Medical).

Measurement of Murine PS Antigen and TAT Complexes by ELISA

Wells from 96-well plates (Maxisorb, Thermo) were coated with 50 μL per well of 10 μg/mL of rabbit polyclonal anti-human PS (DAKO Cytomation) and incubated overnight at 4° C. After 3 washes with TBS buffer (0.05 M tris(hydroxymethyl)aminomethane, 0.15 M NaCl, pH 7.5, 0.05% Tween 20), the plate was blocked with TBS-BSA 2%. Diluted plasma samples (dilution range: 1:300-1:600) were added to the wells and incubated at RT for 2 h. After 3 washed, 50 μL of 1 μg/mL biotinylated chicken polyclonal anti-murine protein S were added and incubated for 2 h at RT. Signal was amplified by streptavidin-HRP conjugated horseradish peroxidase (Thermo) was added and plates incubated for 1 h. The plates were washed 3 times and 100 μLTMB substrate (KPL) was added. Reactions were stopped by adding 100 μL HCl (1M). Absorbance was measure at 450 nm. Standard curves were set up by using serial dilution of pooled normal plasma obtained from 14 healthy mice (8 males and 6 females, 7-12 weeks old). Results were expressed in percentage relative to the pooled normal plasma.

TAT level was measured in duplicate for each plasma sample using a commercially available ELISA (Enzygnost TAT micro, Siemens), according to the manufacturer's instructions.

Mouse Tissue Processing and Sectioning, Immunohistochemistry and Microscopy

Tissue sections (4 μm) with no pre-treatment were stained with hematoxylin/eosin or Masson Trichrome or immunostained for insoluble fibrin, PS or TFPI. The following antibodies were used: fibrin (mAb clone 102-10)[1] final concentration 15.6 μg/mL, incubation for 30 min at RT, secondary antibody rabbit anti-human, (ab7155 Abcam, Cambridge, UK) 1:200 dilution, incubation for 30 min at RT; PS (MAB 4976, R&D, dilution 1:50) incubation for 30 min at RT, secondary antibody rabbit anti-rat, (ab7155 Abcam)-1:200 dilution, incubation for 30 min at RT; TFPI (PAHTFPI-S, Hematological Technologies) final concentration 18.6 μg/mL, incubation for 30 min at RT, secondary antibody rabbit anti-sheep IgG (ab7106, Abcam) 1:200 dilution, incubation for 30 min at RT. All the stainings were performed with the immunostainer BOND RX (Leica Biosystems, Muttenz, Switzerland) following manufacturer's instructions. Whole slides were scanned using 3D HISTECH Panoramic 250 Flash II, with 20× (NA 0.8), 40× (NA 0.95) air objectives. Images processing was done using Panoramic Viewer software.

In Vivo Administration of FVIII to Mice with Complete Genetic Loss of F8

Mice, aged 6-9 week, were anesthetized with ketamine (80 mg/kg) and xylazine (16 mg/kg). We administered intravenously either 0.3 U/kg of recombinant FVIII (Advate®, Baxalta) to reach a FVIII level of 100% at 1 h (normal dose) or an overdose of recombinant FVIII (2 U/kg) to reach >200% at 1 h. Either the normal dose or the overdose was injected 1 h before and 1 h after the introduction of a jugular vein catheter (Mouse JVC 2Fr PU 10 cm, Instech) and then 4 h, 8 h and 16 h after the placement of the central line. Mice were sacrificed 24 h after the first injection. Blood was drawn and organs were harvested. FVIII, fibrinogen and thrombin-antithrombin complexes (TAT) were measured as described in the examples. Lungs were isolated, fixed in 4% paraformaldehyde (PFA) and embedded in paraffin.

FeCl₃ Injury Thrombosis Model in Mesenteric Arteries

A model of thrombosis in mesenteric arteries using intravital microscopy was performed according to reference[2] with minor modifications. Mice were anesthetized by intraperitoneal injection of a mixture of ketamine (80 mg/kg) and xylazine (16 mg/kg). Platelets were directly labeled in vivo by the injection of 100 μL rhodamine 6G (1.0 mM). After selection of the studied field, vessel wall injury was generated by a filter paper (1 mm diameter patch of 1M Whatmann paper) saturated with 10% FeCl₃ applied topically for 1 min. Thrombus formation was monitored in real time under a fluorescent microscope (IV-500, Micron instruments, San Diego, Calif.) with an FITC filter set, equiped with an affinity corrected water-immesion optics (Zeiss, Germany). The bright fluorescent labelled platelets and leucocytes allowed the observation of 1355 μm×965 μm field of view through video triggered stroboscopic epi-illumination (Chadwick Helmuth, El Monte, Calif.). A 10× objective Zeiss Plan-Neofluar with NA0.3. was used. All scenes were recorded on video-tape using a customized low-lag silicon-intensified target camera (Dage MTI, Michigan city, Ind.), a time base generator and a Hi-8 VCR (EV, C-100, Sony, Japan). Time to vessel wall occlusion was measured, as determined by cessation of the blood cell flow.

Fibroblast-Like Synoviocytes (FLS) Isolation, Culture and Flow Cytometry

Murine FLS from 8-10 weeks old mice were isolated and cultured according to[3]. After three passages, phase contrast images of cells were taken, and cells were incubated with FITC-conjugated rat anti-mouse CD11b antibody (M1/70, Pharmingen, BD Biosciences), PE-conjugated rat anti-mouse CD90.2 antibody (30-H12, Pharmingen, BD Biosciences), FITC-conjugated rat anti-mouse CD106 antibody (429 MVCAM.A, Pharmingen, BD Biosciences), PE-conjugated hamster anti-mouse CD54 antibody (3E2, Pharmingen, BD Biosciences), and fluorochrome-conjugated isotype control antibodies for 30 min at 4° C. in the dark. After a final washing and centrifugation step, all incubated cells were analyzed on an LSR II flow cytometer (BD Biosciences) and FACS Diva 7.0 software (BD Biosciences). Human FLS from healthy individual and OA patient were purchased from Asterand, Bioscience and cultured according to manufacture instructions.

Western Blotting

PS and TFPI were detected in human and mouse samples by sodium dodecyl sulfate-polyacrylamide gel electrophoresis (12% gradient SDS-PAGE, Bio-Rad) under reducing conditions. The proteins were transferred to nitrocellulose membranes (Bio-Rad), and then visualized using: 2 ug/mL monoclonal MAB-4976 (R&D system) for murine PS, 1 μg/mL polyclonal AF2975 for murine TFPI (R&D system). Recombinant murine PS[4] (30 ng), recombinant human TFPI full length (provided by T. Hamuro, Kaketsuken, Japan), lysate of washed platelets, PFP from F8$^{-/-}$Pros1$^{+/+}$ mice and placenta lysates from F9$^{+/+}$Pros1$^{+/+}$ mice were used as PS, TFPIα controls. Samples from confluent murine and human FLS conditioned media were collected after 24 h-incubation in a serum-free media (OptiMem) and concentrated 40 times using Amicon filter devices (Millipore, 10 kDa cut-off). For TFPI western blotting, samples were treated with a mixture of five protein deglycosidases (PNGase F, O-Glycosidase, Neuraminidase, β1-4 Galactosidase, β-N-Acetylglucosaminidase, Deglycosylation kit, V4931, Promega) for 12 h at 37° C. before being loaded on the gel. Final detection was completed by using a horseradish peroxidase-conjugated secondary antibody (Dako) and the Supersignal West Dura Extended Duration Chemiluminescence Substrate (Pierce), monitored with a Fuji LAS 3000IR CCD camera.

Immunohistochemistry on Human Knee Synovium

Paraffin-embedded specimens of synovial tissue from twelve HA patients and four HB patients who underwent arthroplasty for severe knee arthropathy were collected at the archives of the Section of Anatomy and Histology, Department of Experimental and Clinical Medicine, University of Florence, as described elsewhere[5,6]. Seven HA patients were treated on demand and five with secondary prophylaxis. All four HB patients were treated on demand. Synovial samples from seven osteoarthritis (OA) patients were used as controls[5,6]. For immunohistochemistry analysis, synovial tissue sections (5 μm thick) were deparaffinized, rehydrated, boiled for 10 minutes in sodium citrate buffer (10 mM, pH 6.0) for antigen retrieval and subsequently treated with 3% H₂O₂ in methanol for 15 min at room temperature to block endogenous peroxidase activity. Sections were then washed in PBS and incubated with Ultra V block (UltraVision Large Volume Detection System Anti-Polyvalent, HRP, catalog number TP-125-HL, LabVision) for 10 min at RT according to the manufacturer's protocol. After blocking non-specific site binding, slides were incubated overnight at 4° C. with rabbit polyclonal anti-human Protein S/PROS1 antibody (1:50 dilution, catalog number NBP1-87218, Novus Biologicals) or sheep polyclonal anti-human Tissue Factor Pathway Inhibitor (TFPI) antibody (1:500 dilution, catalog number PAHTFPI-S, Haematologic Technologies) diluted in PBS. For PS immunostaining, tissue sections were then incubated with biotinylated secondary antibodies followed by streptavidin peroxidase (UltraVision Large Volume Detection System Anti-Polyvalent, HRP; LabVision) according to the manufacturer's protocol. For TFPI immunostaining, tissue sections were instead incubated with HRP-conjugated donkey anti-sheep IgG (1:1000 dilution; catalog number ab97125; Abcam) for 30 min. Immunoreactivity was developed using 3-amino-9-ethylcarbazole (AEC kit, catalog number TA-125-SA; LabVision) as chromogen. Synovial sections were finally counterstained with Mayer's hematoxylin (Bio-Optica), washed, mounted in an aqueous mounting medium and observed under a Leica DM4000 B microscope (Leica Microsystems). Sections not exposed to primary antibodies or incubated with isotype-matched and concentration-matched non-immune IgG (Sigma-Aldrich) were included as negative controls for antibody specificity. Light microscopy images were captured with a Leica DFC310 FX 1.4-megapixel digital colour camera equipped with the Leica software application suite LAS V3.8 (Leica Microsystems).

Fibrin Clot Ultrastructure Investigation

Fibrin clots were prepared at 37° C. from PFP by the addition of ~5 nM TF (Dade Innovin, Siemens). They were then fixed in 2% glutaraldehyde, dehydrated, dried and sputter-coated with gold palladium for visualization using scanning electron microscopy, accordingly to Zubairova et al[7]. Semi quantitative evaluation of network density and fibers branching were performed using STEPanizer software (www.stepanizer.com).

Calibrated Automated Thrombography Assays in Murine Samples

Thrombin generation in PFP and PRP was determined using the calibrated automated thrombogram (CAT) method.

TFPI dependent PS activity was assessed in PRP (150 G/L), as follows. Briefly, 10 µL mouse PRP (150 G/L) was mixed with 10 µL PRP reagent (Diagnostica Stago), and 30 µL of buffer A (25 mm Hepes, 175 mm NaCl, pH 7.4, 5 mg/mL BSA). Thrombin generation was initiated at 37° C. with 10 µL of a fluorogenic substrate/$CaCl_2$ mixture. Final concentrations were as follows: 16.6% mouse plasma, 1 pM hrTF, 4 µM phospholipids, 16 mM $CaCl_2$, and 0.42 mM fluorogenic substrate.

APC dependent PS activity was assessed in a CAT-based APC resistance test in mouse PFP and PRP in accordance to Dargaud Y et al[8]. PRP (150 G/L) was previously activated using 40 µM $Ca^{2+}$ ionophore (A23187) for 5 min at 37 C. Final concentrations were as follows: 16.6% mouse plasma, 22 µM A23187, 1 pM hrTF, 4 µM phospholipids, 2 nM (for PFP) or 8 nM (for PRP) wild type recombinant mouse APC (wt-rmAPC)[5] or mutated recombinant mouse APC (rmAPC L38D), 16 mM $CaCl_2$, and 0.42 mM fluorogenic substrate. The generation and characterization of rmAPC L38D was performed according to ref[9,10] and the purification according to ref[11,12].

For TF titration on PFP, the following reagents were used: PPP reagent and MP reagent (Diagnostica Stago).

Fluorescence was measured using a Fluoroscan Ascent® fluorometer, equipped with a dispenser. Fluorescence intensity was detected at wavelengths of 390 nm (excitation filter) and 460 nm (emission filter). A dedicated software program, Thrombinoscope® version 3.0.0.29 (Thrombinoscope bv) enabled the calculation of thrombin activity against the calibrator (Thrombinoscope bv) and displayed thrombin activity with the time. All experiences were carried out in duplicate at 37° C. and the measurements usually lasted 60 min.

CAT Assay in Human Samples

Written informed consent was obtained from patients. Venous blood was drawn by venipuncture in 3.2% sodium citrate (vol/vol) and centrifuged at 2000 g for 5 min. Platelet-poor plasma (PPP) was then centrifuged at 10000 g for 10 min to obtain PFP. PFP was aliquoted, snap-frozen, and stored at −80° C. until use. For PRP, blood was centrifuged at 180 g×10 min. All subjects gave informed consent to participation. Thrombin generation was assessed in human PFP and PRP, according to ref[13] with minor changes. Briefly, 68 µL PFP or PRP (150 G/L) was incubated for 15 min at 37° C. with 12 µL of either a polyclonal rabbit anti-human PS-IgG antibody (0.42 mg/mL, Dako) or monoclonal antibodies against TFPI (0.66 µm, MW1848, Sanquin) or buffer A. Coagulation was initiated with 20 µL of a 7:1 mixture of the PPP low and PPP 5 pm reagents (Diagnostica Stago) for PFP samples or with PRP reagent (Diagnostica stago) for PRP samples. After addition of 20 µL of $CaCl_2$ and fluorogenic substrate (I-1140; Bachem), the thrombin generation was followed in a Fluoroskan Ascent reader (Thermo Labsystems).

Discussion

PS being is a key regulator of thrombin generation, we considered that targeting PS could constitute a potential therapy for hemophilia.

Extensive studies in mice provide proof of concept data supporting a central role for PS and TFPI as contributing to bleeding and serious joint damage in hemophilic mice. Targeting Pros1 or inhibiting PS has the ability to ameliorate hemophilia in mice as judged by the in vivo improvement of the bleeding phenotype in the tail bleeding assays and the full protection against hemarthrosis (FIGS. 3A-C and 4). Because joints display a very weak expression of TF and synovial cells produce a high amount of TFPIα and PS (FIG. 5), the activity of the extrinsic pathway is greatly reduced intra-articularly, predisposing hemophilic joints to bleed. Moreover, both thrombomodulin (TM) and endothelial protein C receptor (EPCR) are expressed by FLS, suggesting that the TM-thrombin complex activates EPCR bound-PC to generate the very potent anticoagulant, APC, in the context of AH. Importantly, the expression of TFPIα is upregulated by thrombin (FIG. 5F). Thus, AH that usually results in marked local inflammation and joint symptoms that can last for days to weeks also promotes the local generation and secretion of multiple anticoagulants, namely APC, TFPIα, and their mutual cofactor PS, that could help explain the pathophysiology of joint damage in hemophilia.

Figure 6:
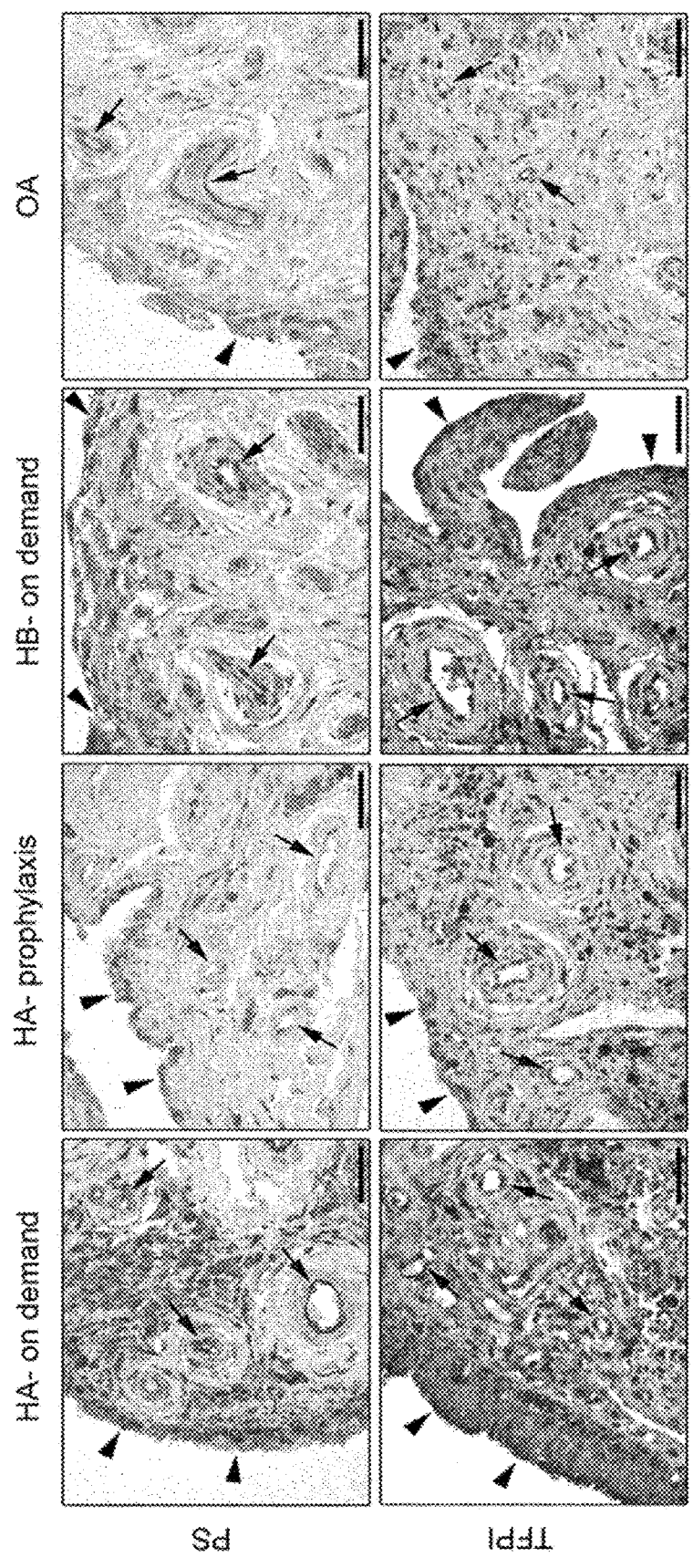
FIG. 6 shows PS and TFPI in human synovium. A, PS and TFPI are expressed in synovial tissue of patients with HA (on demand and on prophylaxis), HB on demand or osteoarthritis (OA). Arrowheads point to synovial lining layer and arrows, to vascular structures in the sublining layer, all positive for both PS and TFPI. Scale bars: 50 µm. B, Western blot analysis of conditioned media of primary human FLS (hFLS) cultures from an healthy individual and an OA patient before and after deglycosylation using anti-TFPI antibody. Human platelet lysate (hPLT) was used as positive control for TFPIα. Blots are representative of three independent experiments.

Observations using clinical samples from hemophilic patients are consistent with the lessons learned from murine studies. In humans, blocking PS in plasma from patients with HA with or without inhibitors normalizes the ETP (FIG. 7D-G). Patients with HB display less intra-articular expression of TFPI and PS than patients with HA, consistent with current knowledge that patients with HB bleed less than those with HA (FIG. 6). Moreover, patients with HA receiving prophylaxis display less TFPI and PS synovial expression than patients receiving FVIII concentrates only in the context of bleeding, i.e., so called "on demand therapy" (FIG. 6A). Finally, human FLS secrete both TFPIα and PS as observed in mice, thus strengthening the extrapolation of murine hemophilia data to humans.

The extensive findings in this report lead us to propose that targeting PS may potentially be translated to therapies useful for hemophilia. PS in human and murine joints is a novel pathophysiological contributor to hemarthrosis and constitutes an attractive potential therapeutic target especially because of its dual cofactor activity for both APC and TFPIα within the joints. In the presence of PS, hemarthrosis increases TFPIα expression in the synovia. Targeting PS in mice protects them from hemarthrosis. Thus, we propose that TFPIα and its cofactor PS, both produced by FLS, together with the TM-EPCR-PC pathway, comprise a potent intra-articular anticoagulant system that has an important pathologic impact on hemarthrosis. The murine PS silencing RNA that we successfully used in hemophilic mice (FIG. 4H-I and FIG. 5A) is a therapeutic approach that we would develop for hemophilic patients. The advantage of silencing RNA over current factor replacement therapy is its longer half-life reducing the frequency of the injections and its possible subcutaneous administration route.

REFERENCES

1. Hisada Y, Yasunaga M, Hanaoka S, et al. Discovery of an uncovered region in fibrin clots and its clinical significance. Sci Rep. 2013; 3:2604.
2. Angelillo-Scherrer A, Fontana P, Burnier L, et al. Connexin 37 limits thrombus propensity by downregulating platelet reactivity. Circulation. 2011; 124(8):930-939.
3. Armaka M, Vassiliki G, Kontoyiannis D, Kollias G. A standardized protocol for the isolation and culture of normal and arthritogenic murine synovial fibroblasts Protocol Exchange. 2009.
4. Fernandez J A, Heeb M J, Xu X, Singh I, Zlokovic B V, Griffin J H. Species-specific anticoagulant and mitogenic activities of murine protein S. Haematologica. 2009; 94(12):1721-1731.
5. Melchiorre D, Linari S, Manetti M, et al. Clinical, instrumental, serological and histological findings suggest that hemophilia B may be less severe than hemophilia A. Haematologica. 2016; 101(2):219-225.
6. Melchiorre D, Milia A F, Linari S, et al. RANK-RANKL-OPG in hemophilic arthropathy: from clinical and imaging diagnosis to histopathology. J Rheumatol. 2012; 39(8):1678-1686.
7. Zubairova L D, Nabiullina R M, Nagaswami C, et al. Circulating Microparticles Alter Formation, Structure, and Properties of Fibrin Clots. Sci Rep. 2015; 5:17611.
8. Dargaud Y, Luddington R, Gray E, et al. Standardisation of thrombin generation test—which reference plasma for TGT? An international multicentre study. Thromb Res. 2010; 125(4):353-356.
9. Harmon S, Preston R J, Ni Ainle F, et al. Dissociation of activated protein C functions by elimination of protein S cofactor enhancement. J Biol Chem. 2008; 283(45):30531-30539.
10. Preston R J, Ajzner E, Razzari C, et al. Multifunctional specificity of the protein C/activated protein C Gla domain. J Biol Chem. 2006; 281(39):28850-28857.
11. Burnier L, Fernandez J A, Griffin J H. Antibody SPC-54 provides acute in vivo blockage of the murine protein C system. Blood Cells Mol Dis. 2013; 50(4):252-258.
12. Mosnier L O, Yang X V, Griffin J H. Activated protein C mutant with minimal anticoagulant activity, normal cytoprotective activity, and preservation of thrombin activable fibrinolysis inhibitor-dependent cytoprotective functions. J Biol Chem. 2007; 282(45):33022-33033.
13. Maurissen L F, Castoldi E, Simioni P, Rosing J, Hackeng T M. Thrombin generation-based assays to measure the activity of the TFPI-protein S pathway in plasma from normal and protein S-deficient individuals. J Thromb Haemost. 2010; 8(4):750-758.
14. Polderdijk S G, Adams T E, Ivanciu L, Camire R M, Baglin T P, Huntington J A. Design and characterization of an APC-specific serpin for the treatment of hemophilia. Blood. 2016.
15. Sailer F, Brisset A C, Tchaikovski S N, et al. Generation and phenotypic analysis of protein S-deficient mice. Blood. 2009; 114(11):2307-2314.
16. Bi L, Lawler A M, Antonarakis S E, High K A, Gearhart J D, Kazazian H H, Jr. Targeted disruption of the mouse factor VIII gene produces a model of haemophilia A. Nat Genet. 1995; 10(1):119-121.
17. Lin H F, Maeda N, Smithies O, Straight D L, Stafford D W. A coagulation factor I X-deficient mouse model for human hemophilia B. Blood. 1997; 90(10):3962-3966.
18. Weiss E J, Hamilton J R, Lease K E, Coughlin S R. Protection against thrombosis in mice lacking PAR3. Blood. 2002; 100(9):3240-3244.

The invention claimed is:

1. A method for treating hemophilia in a subject in need thereof, the method comprising administering to the subject an siRNA against Protein S, said siRNA comprising 17-24 nucleotides and comprising a hybridizing sequence having 100% sequence identity to a corresponding portion of a sequence that is the reverse complement of SEQ ID NO: 001, said siRNA being capable of mediating RNA interference of Protein S when administered to a Protein S-expressing cell.

2. The method of claim 1, wherein said hybridizing sequence comprises deoxynucleotides, phosphothioate deoxynucleotides, phosphothioate ribonucleotides and/or 2'-O-methyl-modified phosphothioate ribonucleotides.

3. The method of claim 1, wherein said siRNA is a double-stranded siRNA.

4. The method of claim 1, wherein said siRNA comprises a hybridizing sequence having 100% sequence identity to a corresponding portion of a sequence that is the reverse complement of SEQ ID NO: 004 or SEQ ID NO: 017.

5. The method of claim 1, said siRNA comprising a hybridizing sequence having 100% sequence identity to a corresponding portion of a sequence that is the reverse complement of nucleotides 501-600 or 2201-2300 of SEQ ID NO: 001.

6. The method of claim 1, wherein said siRNA comprises a hybridizing sequence comprising or consisting of SEQ ID NO: 028 (siRNA_10), SEQ ID NO: 029 (siRNA_11), SEQ ID NO: 030 (siRNA_12), SEQ ID NO: 056 (siRNA_38).

7. The method of claim 1, wherein said siRNA is directed against an intronic sequence of Protein S.

8. The method of claim 1, wherein the hemophilia is selected from hemophilia A, hemophilia B, and hemophilia C.

9. A method for improving thrombin generation in a subject in need thereof, said method comprising administering an siRNA against Protein S, said siRNA comprising 17-24 nucleotides and comprising a hybridizing sequence having 100% sequence identity to a corresponding portion of a sequence that is the reverse complement of SEQ ID NO: 001, said siRNA being capable of mediating RNA interference of Protein S when administered to a Protein S-expressing cell.

10. The method of claim 9, wherein said hybridizing sequence comprises deoxynucleotides, phosphothioate deoxynucleotides, phosphothioate ribonucleotides and/or 2'-O-methyl-modified phosphothioate ribonucleotides.

11. The method of claim 9, wherein said siRNA is a double-stranded siRNA.

12. The method of claim 9, wherein said siRNA comprises a hybridizing sequence having 100% sequence identity to a corresponding portion of a sequence that is the reverse complement of SEQ ID NO: 004 or SEQ ID NO: 017.

13. The method of claim 9, said siRNA comprising a hybridizing sequence having 100% sequence identity to a corresponding portion of a sequence that is the reverse complement of nucleotides 501-600 or 2201-2300 of SEQ ID NO: 001.

14. The method of claim 9, wherein said siRNA comprises a hybridizing sequence comprising or consisting of SEQ ID NO: 028 (siRNA_10), SEQ ID NO: 029 (siRNA_11), SEQ ID NO: 030 (siRNA_12), SEQ ID NO: 049 (siRNA_31), or SEQ ID NO: 056 (siRNA_38).

15. The method of claim 9, wherein said siRNA is directed against an intronic sequence of Protein S.

16. A method for reducing the expression of Protein S in a cell, the method comprising administering an siRNA said siRNA comprising 17-24 nucleotides and comprising a hybridizing sequence having 100% sequence identity to a corresponding portion of a sequence that is the reverse complement of SEQ ID NO: 001, said siRNA being capable of mediating RNA interference of Protein S when administered to a Protein S-expressing cell.

17. The method of claim 16, wherein said hybridizing sequence comprises deoxynucleotides, phosphothioate deoxynucleotides, phosphothioate ribonucleotides and/or 2'-O-methyl-modified phosphothioate ribonucleotides.

18. The method of claim 16, wherein said siRNA is a double-stranded siRNA.

19. The method of claim 16, wherein said siRNA comprises a hybridizing sequence having 100% sequence identity to a corresponding portion of a sequence that is the reverse complement of SEQ ID NO: 004 or SEQ ID NO: 017.

20. The method of claim 16, wherein said siRNA comprises a hybridizing sequence having 100% sequence identity to a corresponding portion of a sequence that is the reverse complement of nucleotides 501-600 or 2201-2300 of SEQ ID NO: 001.

21. The method of claim 16, wherein said siRNA comprises a hybridizing sequence comprising or consisting of SEQ ID NO: 028 (siRNA_10), SEQ ID NO: 029 (siRNA_11), SEQ ID NO: 030 (siRNA_12), SEQ ID NO: 049 (siRNA_31), or SEQ ID NO: 056 (siRNA_38).

22. The method of claim 16, wherein said siRNA is directed against an intronic sequence of Protein S.

* * * * *